US012773439B2

(12) United States Patent
Li

(10) Patent No.: US 12,773,439 B2
(45) Date of Patent: Oct. 27, 2026

(54) BOTANICAL EXTRACTION

(71) Applicant: Performance Labs Pte. Ltd., Singapore (SG)

(72) Inventor: Dan Li, Singapore (SG)

(73) Assignee: PERFORMANCE LABS PTE. LTD., Singapore (SG)

( * ) Notice: Subject to any disclaimer, the term of this patent is extended or adjusted under 35 U.S.C. 154(b) by 783 days.

(21) Appl. No.: 18/186,687

(22) Filed: Mar. 20, 2023

(65) Prior Publication Data

US 2023/0302073 A1 Sep. 28, 2023

Related U.S. Application Data

(60) Provisional application No. 63/371,338, filed on Aug. 12, 2022, provisional application No. 63/269,758, filed on Mar. 22, 2022.

(51) Int. Cl.

| | |
|---|---|
| ***A61K 36/185*** | (2006.01) |
| ***A61K 31/192*** | (2006.01) |
| ***A61K 31/522*** | (2006.01) |
| ***A61K 47/12*** | (2006.01) |
| ***A61K 47/18*** | (2017.01) |

(52) U.S. Cl.

CPC .......... *A61K 36/185* (2013.01); *A61K 31/192* (2013.01); *A61K 31/522* (2013.01); *A61K 47/12* (2013.01); *A61K 47/186* (2013.01); *A61K 2236/33* (2013.01); *A61K 2236/331* (2013.01); *A61K 2236/37* (2013.01); *A61K 2236/53* (2013.01)

(58) Field of Classification Search

CPC .. A61K 36/185; A61K 31/192; A61K 31/522; A61K 47/12; A61K 47/186; A61K 2236/33; A61K 2236/331; A61K 2236/37; A61K 2236/53

See application file for complete search history.

(56) References Cited

U.S. PATENT DOCUMENTS

| | | | |
|---|---|---|---|
| 2015/0189898 | A1 | 7/2015 | Deuchi et al. |
| 2016/0113987 | A1 | 4/2016 | Choi et al. |
| 2016/0213042 | A1 | 7/2016 | Takeuchi et al. |
| 2021/0205394 | A1 | 7/2021 | Lavaud et al. |
| 2021/0337850 | A1 | 11/2021 | Solá Parera et al. |

FOREIGN PATENT DOCUMENTS

| | | | |
|---|---|---|---|
| WO | WO 99/61038 | A1 | 12/1999 |
| WO | WO 2007/010478 | A2 | 1/2007 |
| WO | WO 2020/254579 | A1 | 12/2020 |

OTHER PUBLICATIONS

International Search Report and Written Opinion issued in application No. PCT/US2023/64717, mailed Aug. 24, 2023.

Rebocho et al., "Fractionated extraction of polyphenols from mate tea leaves using a combination of hydrophobic / hydrophilic NADES," Current Research in Food Science, Mar. 15, 2022, in 10 pages.

*Primary Examiner* — Robert A Wax
*Assistant Examiner* — Quanglong N Truong
(74) *Attorney, Agent, or Firm* — Knobbe, Martens, Olson & Bear, LLP

(57) ABSTRACT

Methods for extracting compounds of interest from a botanical material are disclosed herein. The methods include identifying optimal natural deep eutectic solvents (NaDESs), mixing the identified NaDESs with a botanical material, and isolating compounds of interest from the mixture. Also described are compositions that include the isolated compounds of interest with NaDESs.

10 Claims, 13 Drawing Sheets

Caffeine

Theobromine

Caffeic Acid

Chlorogenic Acid 4,5-dicaffeoylquinic acid 3,5-dicaffeoylquinic acid 3,4-dicaffeoylquinic acid 4-caffeoylquinic acid Rutin Luteolin-diglucoside 5-O-caffeoylquinic acid Ursonic Acid Glycosides

| Saponin | Moiety | R | $R_1$ | $R_2$ | $R_3$ |
|---|---|---|---|---|---|
| Matesaponin 1 | Ursolic acid | glc(1→3)ara | H | glc | H |
| Matesaponin 2 | Ursolic acid | glc(1→3)rha(1→2)ara | H | glc | H |
| Matesaponin 3 | Ursolic acid | glc(1→3)ara | H | glc(1→6)glc | H |
| Matesaponin 4 | Ursolic acid | glc(1→3)rha(1→2)ara | H | glc(1→6)glc | H |
| Matesaponin 5 | Ursolic acid | glc(1→3)rha(1→2)ara | H | glc(1→4)glc(1→6)glc | H |

BOTANICAL EXTRACTION

RELATED APPLICATIONS

This application claims the benefit of priority to U.S. Provisional Patent Application Nos. 63/269,758, filed Mar. 22, 2022 and 63/371,338, filed Aug. 12, 2022, the disclosures of which are incorporated by reference herein in their entireties.

FIELD

The present disclosure relates generally to the field of plant extraction processes. In particular, the disclosure relates to methods for extracting compounds from a botanical, such as yerba mate, and compositions that include botanical extracts with natural deep eutectic solvents. The methods include precision determination and modeling of bio-inspired natural deep eutectic solvents for improved extraction of compounds from botanicals.

BACKGROUND

*Ilex paraguariensis* (yerba mate) is a medicinal plant that includes numerous bioactive compounds, including chlorogenic acid, saponins, and xanthine alkaloids. Traditional extraction of these compounds from yerba mate uses harsh processes and chemicals that are not environmentally friendly or efficient.

Natural deep eutectic solvents (NaDESs) are ubiquitous compounds that solubilize various metabolites and compounds, and are environmentally friendly.

SUMMARY

The present disclosure generally relates to compositions that include botanical extracts with natural deep eutectic solvents, and methods of purifying botanical extracts using the natural deep eutectic solvents.

Some embodiments provided herein relate to methods of isolating a plant extract from a plant material. In some embodiments, the methods include obtaining a plant material. In some embodiments, the methods include processing the plant material. In some embodiments, the methods include mixing the processed plant material with a natural deep eutectic solvent (NaDES). In some embodiments, the methods include isolating a plant extract. In some embodiments, the plant material is obtained from yerba mate. In some embodiments, the NaDES includes choline chloride, citric acid, glucose, sucrose, or a combination thereof. In some embodiments, the NaDES includes choline chloride and citric acid. In some embodiments, the choline chloride and citric acid are present in a ratio of 3:1. In some embodiments, the NaDES includes water in an amount ranging from 10% to 80%. In some embodiments, the plant extract is a xanthine alkaloid, chlorogenic acid, or matesponin. In some embodiments, the xanthine alkaloid includes caffeine, theobromine, theophylline, or an analogue or derivative thereof. In some embodiments, the chlorogenic acid includes caffeic acid, tannin, or an analogue or derivative thereof. In some embodiments, the methods further include heating, stirring, centrifuging, and/or filtering following the mixing step. In some embodiments, the NaDES includes choline chloride and citric acid present in a ratio of 3:1, and water present in an amount of 50%.

Some embodiments provided herein relate to compositions. In some embodiments, the compositions include botanical isolates and a natural deep eutectic solvent (NaDES). In some embodiments, the botanical isolates includes isolates from yerba mate. In some embodiments, the botanical isolates include a xanthine alkaloid, chlorogenic acid, or matesponin. In some embodiments, the botanical isolates include caffeine, theobromine, theophylline, caffeic acid, tannin, or an analogue or derivative thereof. In some embodiments, the NaDES includes choline chloride, citric acid, glucose, sucrose, or a combination thereof. In some embodiments, the NaDES includes choline chloride and citric acid. In some embodiments, the choline chloride and citric acid are present in a ratio of 3:1. In some embodiments, the compositions include caffeine, theobromine, theophylline, caffeic acid, tannin, or an analogue or derivative thereof, choline chloride and citric acid present in a ratio of 3:1, and 50% water.

These features, together with other features herein further explained, are described in greater detail in the following description of the drawings and detailed description.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are therefore, not to be considered limiting of its scope, the disclosure will be described with additional specificity and detail through use of the accompanying drawings.

FIG. 6A depicts a graph of model predicted value vs actual value of total extraction yield of yerba mate extracts. FIG. 6B depicts response surface and contour plots showing effect of extraction temperature (A), liquid/solid ratio (B), and extraction time (C) on the extraction yield of total extracts from yerba mate. Comparison of model prediction and actual values for chlorogenic acid is shown in FIG. 6C. Results of extraction yield of chlorogenic acid from yerba mate as affected by extraction temperature, liquid/solid ration, and time are shown in FIG. 6D.

DETAILED DESCRIPTION

Figure 1A:
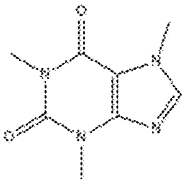
FIGS. 1A-1B illustrate some of the major bioactive components identified in yerba mate.
Figure 1A:
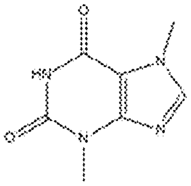
Figure 1A:
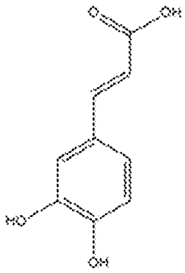
Figure 1A:
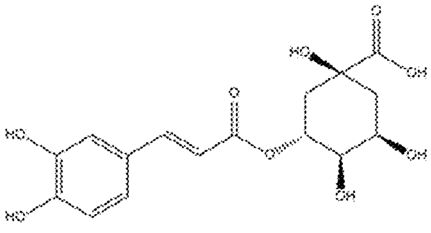
Figure 1A:
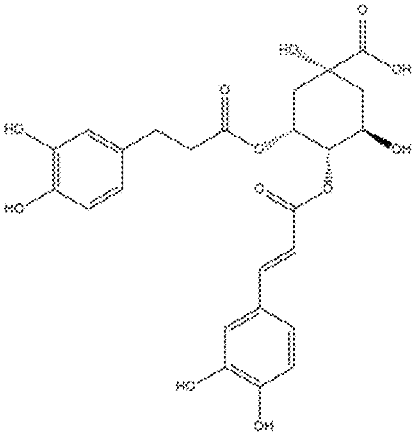
Figure 1A:
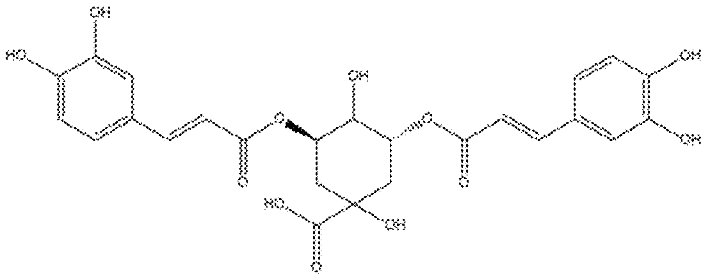
Figure 1A:
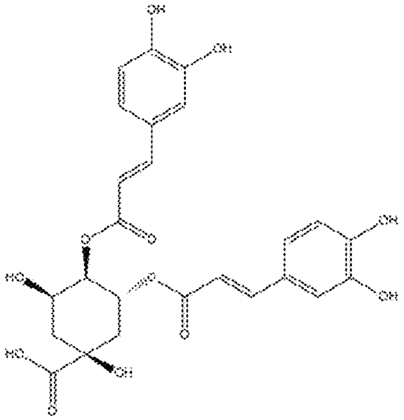
Figure 1A:
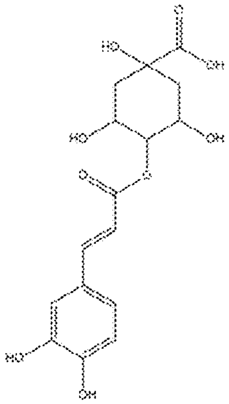
Figure 1A:
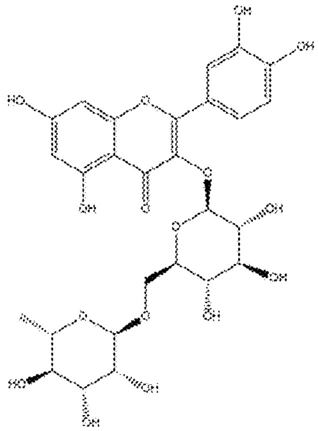

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the drawings, can be arranged, substituted, combined, separated, and designed in a wide variety of different configurations, all of which are explicitly contemplated herein.

As summarized herein, aspects of methods for isolating and extracting compounds from plant materials and the isolated components combined with natural deep eutectic solvents (NaDESs) are provided herein.

It is to be understood that this disclosure is not limited to particular embodiments described, as such may, of course, vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Unless defined otherwise, technical and scientific terms used herein have the same meaning as commonly understood by one of ordinary skill in the art to which the present disclosure belongs. For purposes of the present disclosure, the following terms are defined below.

In some embodiments, provided herein are methods of extracting compounds from plants using one or more NaDES. In some embodiments, the methods include identifying combinations of NaDESs, mixing the NaDESs with plant material, processing the mixture, and extracting compounds from the plant. The extracted compounds may further be isolated.

Also provided herein are compositions that include isolated compounds from a plant in combination with NaDESs that were used to isolate the compounds.

As used herein, the term "plant" has its ordinary meaning as understood in light of the specification, and refers to a whole plant or any parts or derivatives thereof, such as plant cells, plant protoplasts, plant cell tissue cultures from which plants can be regenerated, plant calli, embryos, pollen, ovules, fruit, flowers, leaves, seeds, roots, root tips, and the like. The term "botanical" is used herein interchangeably with plant, and refers to a plant or any parts derived thereof.

In some embodiments, the plant is any plant having components therein that are desirable to extract, purify, or obtain from the plant. For example, the plant is or is derived from maca, he shou wu, iporuru (*Alchornea castaneifolia*), kanna (*Sceletium tortosum*), honokiol (*Magnolia grandiflora*), jujube (*Ziziphi spinosae*), cnidium (*Fructus cnidii*), corydalis (*Corydalis yanhusuo*), albizia (*Cortex albiziae*), ginseng (*Panax ginseng*), polygonum (*Polygoni multiflori*), fu ling (*Poria cocos*), cornus (*Fructus corni*), Chinese yam (*Rhizoma dioscoreae*), muira puama, *Dendrobium* sp., licorice root radix (*Glycyrrhizae preparata*), cordyceps (*Cordyceps sinensis*), Chinese angelica (*Angelicae sinensis*), kratom (*Mitragyna speciosa*), bacopa monnieri, catuaba, ashwaghanda, peganum harmala, wheat, alfalfa, oat, kamut, echinacea, chlorella, amla, stinging nettles, carob, mesquite, chuchuhuasai, clavo huasca, chanca piedra, guayusa, Rhodiola rosea, shilajit, higenamine, moringa (*Moringa oleifera*), horny goat weed (*Epidmedium*), astragalus, aloe vera, turmeric, pine, curcumin (turmeric compound), hops, xanthohumol (hops compound), passion flower, mucuna puriens, tusli, black pepper, bioperine (black pepper compound), Siberian ginseng, American ginseng, yerba mate, lemon balm, astragulus, kava, schizandra, skullcap, valerian, California poppy, epidmedium, pau d'arco, gingko, lotus, lilly, tea, coffee, or cacao, or any components of such plants, including bark, leaves, stems, roots, flowers, fruits, pollens, seeds or the like. Plant ingredients may include plant oils, including, for example linalool; b-caryophyllene; b-myrcene; d-limonene; humulene; a-pinene; ylang (*Cananga odorata*); yarrow (*Achillea millefolium*); violet (*Viola odorata*); vetiver (*Vetiveria zizanoides*); vanilla (*Vanilla plantifolia*); tuberose (*Polianthes tuberosa*); thyme (*Thymus vulgaris* L.); tea tree (*Melaleuca alternifolia*); tangerine (*Citrus reticulata*); spruce (*Picea mariana*); spruce (*Tsuga Canadensis*); zpikenard (*Nardostachys jatamansi*); spearmint (*Mentha spicata*); sandalwood (*Santalum spicatum*); rosewood (*Aniba rosaeodora*); rosemary verbenone (*Rosmarinus officinalis*); rosemary (*Rosmarinus officinalis*); rose (*Rosa damascena*); rose geranium (*Pelargonium roseum*); ravensara (*Ravensara aromatica*); plai (*Zingiber cassumunar*); pine needle (*Pinus sylvestris* L.); petitgrain (*Citrus aurantium*); peppermint (*Mentha piperita*); pepper (*Piper nigrum* L.); patchouli (*Pogostemon cablin*); palo santo (*Bursera graveolens*); palmarosa (*Cymbopogon martini*); osmanthus (*Osmanthus fragrans*); oregano (*Origanum vulgare*); orange (*Citrus sinensis*); oak moss (*Evemia prunastri*); nutmeg (*Myristica fragrans*); niaouli (*Melaleuca viridifloria*); neroli (*Citrus aurantium*); myrtle (*Myrtus communis*); myrrh (*Commiphora myrrha*); mimosa (*Acacia decurrens*); melissa (*Melissa officinalis* L.); marjoram (*Origanum majorana*); manuka (*Leptospermum scoparium*); mandarin (*Citrus deliciosa*); mandarin (*Citrus deliciosa*); lotus (*Nelumbo nucifera*); lotus (*Nelumbo nucifera*); lotus (*Nelumbo nucifera*); lime (*Citrus aurantifolia*); lily (*Lilum aurantum*); lemongrass (*Cymbopogon citratus*); lemon (*Citrus limonum*); lavender (*Lavandula angustifolium*); lavandin (*Lavandula hybrida grosso*); kanuka (*Kunzea ericoides*); juniper (*Juniperus cummunis*); jasmine (*Jasminum officinale*); jasmine (*Jasminum sambac*); helichrysum (*Helichrysum italicum*); grapefruit (*Citrus xparadisi*); grapefruit (*Citrus paradisi*); ginger (*Zingiber officinalis*); geranium (*Pelargonium graveolens*); geranium (*Pelargonium graveolens*, 'Herit); gardenia (*Gardenia jasminoides*); galbanum (*Ferula galbaniflua*); frankincense (*Boswellia carterii*); frangipani (*Plumeria alba*); fir needle white (*Abies alba*); fir needle Siberia (*Abies siberica*); fir needle Canada (*Abies balsamea*); fennel (*Foeniculum vulgare*); Eucalyptus Smithii. Eucalyptus Radiata, Eucalyptus Globulus, Eucalyptus Citriodora, Eucalyptus Blue Mallee (*Eucalyptus polybractea*); elemi (*Canarium luzonicum*); dill (*Anethum graveolens*); cypress (*Cupressus sempervirens*);

cumin (*Cuminum cyminum*); coriander (*Coriandum sativum*); cocoa (*Theobroma cacao*); clove (*Eugenia caryophylatta*); clary sage (*Salvia sclarea*); cistus (Labdanum) (*Cistus ladaniferus* L.); cinnamon (*Cinnamomum zeylanicum*); chamomile (*Anthemis nobilis*); chamomile (*Matricaria chamomilla*); celery seed (*Apium graveolins*); cedarwood (*Thuja plicata*); cedarwood (*Juniperus virginiana*); cedarwood atlas (*Cedrus atlantica*); carrot seed (*Daucus carota*); cardamon (*Elettaria cardamomum*); caraway seed (*Carum carvi*); cajeput (*Melaleuca cajuputi*); cade (*Juniperus oxycedrus*); birch (*Betula alba*); birch (*Betula lenta*); bergamot (*Citrus bergamia*); bay laurel (*Laurus nobilis*); basil (*Ocimum basilicum*); basil (*Ocimum* sanctum); basil (*Ocimum basilicum*); balsam poplar (*Populus balsamifera*); balsam Peru (*Myroxylon balsamum*); or angelica (*Angelica archangelica* L.).

In some embodiments, the plant is yerba mate. As used herein, the term "yerba mate" has its ordinary meaning as understood in light of the specification, and refers to the medicinal plant, *Ilex paraguariensis*. Yerba mate leaves have been traditionally extracted using aqueous mixtures of methanol, ethanol, and/or acetone in conventional solid/liquid extraction. These chemicals and the traditional methods of extraction are harsh, and result in major economic and environmental impacts. With the object of developing environmentally friendly processing, NaDESs are disclosed herein for use in extracting materials from plants, including yerba mate.

*Ilex paraguariensis* is one of the most commercialized medicinal plants of South America, grows naturally and is cultivated in Argentina, Uruguay, Brazil, and Paraguay. The component parts of this plant are used to prepare a tea-like beverage (Croge et al., 2020). Yerba mate also has a long history of use worldwide. In Europe it is used for weight loss, physical and mental fatigue, nervous depression, rheumatic pains, and psychogenic- and fatigue-related headaches. In Germany, it has become popular as a weight-loss aid. Yerba mate is the subject of a German monograph, which lists its approved uses for mental and physical fatigue, and describes it as having analeptic, diuretic, positively inotropic, positively chronotropic, glycogenolytic, and lipolytic effects. In France, yerba mate is approved for the treatment of asthenia (weakness or lack of energy), as an aid in weight-loss programs, and to increase the renal excretion of water. It also appears in the British Herbal Pharmacopoeia (1996), with indications for the treatment of fatigue, weight loss, and headaches. In the U.S., yerba mate was recommended for arthritis, headache, hemorrhoids, fluid retention, obesity, fatigue, stress, constipation, allergies, and hay fever, and is used to cleanse the blood, tone the nervous system, retard aging, stimulate the mind, control the appetite, stimulate the production of cortisone, and is believed to enhance the healing powers of other herbs. Yerba mate is also cultivated in India, and the Indian Ayurvedic Pharmacopoeia lists maté for the treatment of psychogenic headaches, nervous depression, fatigue, and rheumatic pains (Heck & De Mejia, 2007).

Figure 1B:
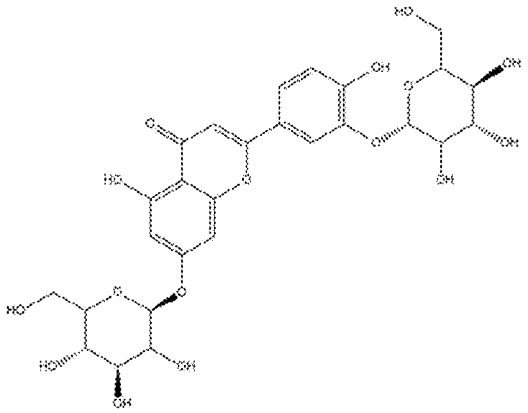
Figure 1B:
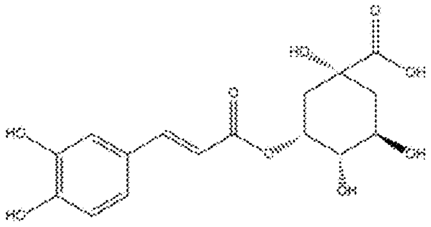
Figure 1B:
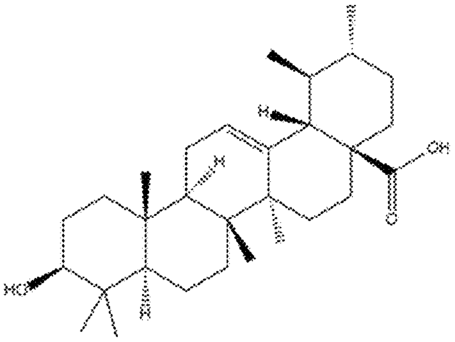
Figure 1B:
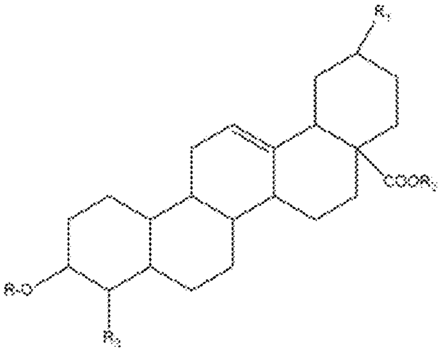

The primary known bio-active chemical constituents of yerba mate include xanthine alkaloids, chlorogenic acids, and matesponins. Xanthine alkaloids include, for example, caffeine (1,3,7-trimethylxanthine), theobromine (3,7-dimethylxanthine), and theophylline (1,3-dimethylxanthine), and analogues or derivatives thereof. Chlorogenic acids include, for example, caffeic acid and tannins, and analogues or derivatives thereof (Oellig et al., 2018). The content of yerba mate leaf has been assayed and reported to contain between 0.7%-2% caffeine by weight, 0.3%-0.9% theobromine by weight, theophylline in relatively minor amounts, saponins, and 10% caffeic acid derivatives (chlorogenic acid, caffeic acid, 3,4-dicaffoylquinic acid, 3,5-dicaffoylquinic acid and 4,5-dicaffoylquinic acid) (Matei et al., 2016). Other chemicals found in yerba mate include alpha-amyrin, alpha-terpineol, arachidic acid, beta-amyrin, butyric acid, 5-o-caffeoylquinic acid, calcium, carotene, choline, chlorophyll, chrysanthemum, cyanidin-3-o-xylosyl-glucoside, cyanidin-3-glucoside, essential oil, eugenol, geraniol, geranyl acetone, guayacan b, indole, inositol, ionone, iso-butyric acid, iso-caproic acid, iso-chlorogenic acid, iso-valeric acid, kaempferol, lauric acid, levulose, linalool, linoleic acid, maté saponins, neochlorogenic acid, nerolidol, nicotinic acid, nudicaucin c, octan-1-ol, octanoic acid, oleic acid, palmitic acid, palmitoleic acid, pyridoxine, quercetin, raffinose, safrole, stearic acid, tannins, theobromine, theophylline, trigonelline, and ursolic acid. In addition, 7%-14% of tannins were also reported in yerba mate leaf material (Bastos et al., 2007; Bojić et al., 2013; Burris et al., 2012; Chandrasekara & Shahidi, 2018; Chianese et al., 2019; Ferreira Cuelho et al., 2015; Frizon et al., 2018; Isolabella et al., 2010; Junior & Morand, 2016; Puangpraphant, 2012; Riachi et al., 2018; Souza et al., 2015). FIGS. 1A and 1B depict major constituents of yerba mate.

Theobromine is used as a vasodilator, a diuretic, and a heart stimulator. Theobromine is recognized as an antagonist of the adenosine receptor and an inhibitor of phosphodiesterase, and may be helpful in the management of fatigue and orthostatic hypotension.

As used herein, the term "extract", "extraction", "extracting", or any derivative thereof has its ordinary meaning as understood in light of the specification, and refers to a process of removing material, compounds, compositions, or other components from a starting material. A process of extraction can be performed by various means, including by physical or chemical extraction, such as by pressing, grinding, heating, stirring, or other known methods for extracting a component from a starting material.

As used herein, the term "isolate", "isolation", "isolating", or any derivative thereof has its ordinary meaning as understood in light of the specification, and refers to a material, such as a component of a plant extract, which is substantially or essentially free from components which normally accompany or interact with the material as found in its naturally occurring environment or substantially or essentially free from components which accompany or interact the material in a processed form, such as in a processed yerba mate material or from a substance used during the isolation process. Where the term "substantially purified" is used, this designation will refer to a composition in which the desired component is the major or primary component of the composition, such as constituting about 50%, about 60%, about 70%, about 80%, about 90%, about 95% or more of the composition (for example, weight/weight and/or weight/volume). As used herein, the term "substantially purified" refers to compounds, such as those derived from yerba mate, that are removed from their natural environment or from a processed form thereof, isolated or separated, and are at least 60% free, such as 60, 65, 70, 75, 80, 85, 90, 95, 96, 97, 98, or 99% free from other components with which they are naturally associated.

As used herein, the term "natural deep eutectic solvent" (NaDES) has its ordinary meaning as understood in light of the specification, and refers to a sugar, amino acid, or organic acid that is typically solid at room temperature, but when combined at a particular molar fraction, present a high melting point depression, becoming a liquid at room temperature.

The discovery of the deep eutectic solvents (DES) is a major breakthrough in the world of green chemistry. Deep eutectic solvents are frequently defined as binary or ternary mixtures of compounds that are able to associate mainly via hydrogen bonds. Combining these compounds at a certain molar ratio results in a eutectic mixture. These solvents are composed of two or more inexpensive nontoxic components, one of them with the capacity to be a hydrogen bond acceptor, while the other possesses the properties of a hydrogen bond donor. Due to the formation of intramolecular hydrogen bonds and Van der Waals interactions, these solvents have much lower melting point than that of its individual components. An example of a deep eutectic is the mixture of hydroxyethyl trimethyl ammonium (choline chloride) (melting point $T_m$=302° C.) with urea ($T_m$=133° C.), which results in a eutectic of very low melting point ($T_m$=12° C.). What is interesting about these solvents is that they are not only liquid at ambient temperature but also tunable and highly solubilizing (Abbott et al., 2004).

Natural deep eutectic solvents (NaDESs) are a particular class of DES, prepared from biomolecules, such as choline chloride and betaine as the organic salt, and urea, organic acids, amino acids, or sugars as the hydrogen bond donor (Dai, 2006, 2007). This category covers the DES that are made of primary metabolites such as organic acids, amino acids, sugars, polyols, and choline derivatives (Dai et al., 2013). In addition, water may also be part of a NaDES composition. Remarkably, NaDESs are ubiquitously present in living organisms both in the intracellular and extracellular media where they may play a role in the synthesis and solubilization of poorly soluble metabolites such as flavonoids, in enzymatic reactivity, and also in drought tolerance. In this paradigm, NaDESs constitute a third type of natural liquid, separated from water and lipids (Choi et al., 2011). A series of NaDESs have been formed from abundant biomolecules, including combinations of choline chloride with citric, malic, maleic, and ascorbic acids; proline with citric acid; malic acid with glucose; and mixtures of sugars (for example, fructose:glucose, fructose:sucrose, glucose:sucrose). NaDESs are regarded as an environmentally friendly alternative solvent for the extraction of biomolecules (Liu et al., 2018).

NaDESs exhibit favorable characteristics as solvents, such as low vapor pressure, nonflammability, low or negligible toxicity, environmentally friendly, ease of preparation, and low cost. As NaDES species exhibit a superior solubilizing ability for natural products, this provides a special advantage for NaDES as extraction media. The most prominent functional groups of NaDES constituents are carboxylic acids, hydroxyl groups, and carbonyl groups. In a NaDES matrix, these groups can form a hydrogen-bonding network via intermolecular interactions that modify their physicochemical environment. Generally, the greater the intermolecular attractions, the larger the polarity. Thus, polarity is generally a solubilization property. The unique intermolecular interactions or arrangements of a NaDES matrix generate its special solubilizing and stabilizing properties. For example, while proline is only sparingly soluble in dimethylsulfoxide (DMSO), a proline-based multiple component NaDES can be fully miscible with the same organic solvent.

NaDESs possess biological activity, and can be designed with specific biologically activity. For example, if a solvent with antioxidative or/and antitumor activity is required, NaDES may be prepared with compounds that possess the desired biological activity. Previously, it was demonstrated that NaDES used for extraction purposes could enhance the antioxidative activities of obtained plant extracts, which could be explained by the reactive oxygen species scavenging activities of the NaDES itself or NaDES forming compounds. The antioxidative activity of these NaDESs was not unexpected because the forming compounds (malic acid, citric acid, proline and betaine) also possess antioxidative activity. Furthermore, since the components of NaDES are abundant in the nature and are part of our daily diet, as well as a food supplement already present on the market (e.g., choline, citric acid, betaine, amino acids, etc.) it is expected that extract obtained by NaDES may be directly used in food, pharmaceutical, cosmetical and agrochemical products without the need for expensive downstream purification steps. NaDES also enhance the biological activity of phenolic acids (Faggian et al., 2016), and may be used directly in food, cosmetic, and pharmaceutical formulations.

NaDESs are ubiquitously present in living organisms both in the intracellular and extracellular media, where they play a role in synthesis and solubilization of poorly soluble metabolites, such as flavonoids. NaDESs also play a role in enzymatic reactivity and in drought tolerance. NaDESs exhibit numerous favorable characteristics, including low vapor pressure, non-flammability, low or negligible toxicity, no negative environmental impact, low cost, and ease of use. Further, the number of structural combinations of NaDESs is enormous, resulting in the ability to optimally design a combination of NaDESs for each specific application. NaDESs are biocompatible, and enhance biological activity. Thus, it is possible to optimally design compositions with NaDESs having a specific biological activity. Extracts obtained by NaDESs and having NaDESs present in the compositions may be used in food, nutraceutical, pharmaceutical, cosmetic, agrochemical, and industrial applications.

Methods described herein relate to processing botanical materials, such as yerba mate plant materials, including whole plant, stem, leaves, or other portions of a plant in improved, efficient, and environmentally friendly methods. In some embodiments, the methods include providing a yerba mate plant material, screening optimal NaDESs, mixing the yerba mate plant material with the NaDESs, and isolating one or more compound of interest of yerba mate.

In some embodiments, the plant material is a raw, unprocessed material, such as a whole plant material directly cultivated. In some embodiments, the plant material is a processed material, such as a dried plant material, a blended plant material, a ground plant material, a crushed plant material, a powdered plant material, a liquid plant material, or any other processed material. In some embodiments, the yerba mate plant material is the whole plant, a leaf, a root, a stem, a flower, bark, or any other portion of the plant.

In some embodiments, the NaDESs includes one or more NaDES, including choline chloride, citric acid, malic acid, maleic acid, ascorbic acid, proline, glucose, sucrose, fructose, or any combination thereof. Combinations of one or more NaDESs can be provided in various ratios, such as 1:1, 1:2, 1:3, 1:4, 2:3, 3:2, 2:1, 3:1, or 4:1 for any two NaDESs, or any combination of these ratios for any three or more NaDESs.

In some embodiments, the one or more NaDESs includes a first NaDES and water, and at least one hydrogen bond donor. In some embodiments, the hydrogen bond donor is an organic acid or a polyol. In some embodiments, the hydrogen bond donor is an organic acid, including, for example, lactic acid, malic acid, maleic acid, pyruvic acid, fumaric acid, succinic acid, citric acid, acetic acid, ursolic acid, tartaric acid, ascorbic acid, malonic acid, oxalic acid, glucuronic acid, neuraminic acid, sialic acid, shikimic acid, phytic acid, galacturonic acid, iduronic acid, hyaluronic acid, hydroxycitric acid, and lactone derivatives. Exemplary combinations of NaDESs are provided in Table 1.

TABLE 1

Exemplary combinations of NaDESs

| Combination | choline chloride (CL) | Citric acid (CIT) | Glucose (GLU) | Sucrose (SUC) | Water |
|---|---|---|---|---|---|
| CITGLU2:1 | | 2 | 1 | | 30% |
| CITGLU1:1 | | 1 | 1 | | 30% |
| CITGLU1:2 | | 1 | 2 | | 30% |
| CITSUC2:1 | | 2 | | 1 | 30% |
| CITSUC1:1 | | 1 | | 1 | 30% |
| CITSUC1:2 | | 1 | | 2 | 30% |
| CLCIT3:1 | 3 | 1 | | | 30% |
| CLCIT2:1 | 2 | 1 | | | 30% |
| CLCIT1:1 | 1 | 1 | | | 30% |
| CLCIT1:2 | 1 | 2 | | | 30% |
| CLCIT1:3 | 1 | 3 | | | 30% |
| CLCIT1:1 | 1 | 1 | | | 50% |
| CLCIT1:1 | 1 | 1 | | | 80% |
| CLGLU1:1 | 1 | | 1 | | 30% |
| CLSUC1:1 | 1 | | | 1 | 30% |
| CITGLU1:1 | | 1 | 1 | | 30% |
| CITSUC1:1 | | 1 | | 1 | 30% |
| CLCITGLU1:1:1 | 1 | 1 | 1 | | 30% |
| CLCITSUC1:1:1 | 1 | 1 | | 1 | 30% |

In some embodiments, the compound of interest isolated from yerba mate is a phenolic acid, a chlorogenic acid, a flavonoid, an alkaloid, a terpene, a fragrance, an antioxidant, or a saponin, or any combination thereof.

In some embodiments, mixing the plant and/or plant material with the NaDES includes immersing, spraying, coating, or contacting the plant and/or plant material with a solution of NaDES. In some embodiments, the methods include heating the mixture, stirring the mixture, macerating the mixture, or impregnating the mixture, or any combination thereof. In some embodiments, the heating the mixture can be performed by heating the mixture to a temperature ranging from about 15° C. to about 80° C., such as 15, 20, 25, 30, 35, 40, 45, 50, 55, 60, 65, 70, 75, or 80° C., or at a temperature within a range defined by any two of the aforementioned values.

In some embodiments, isolating a compound of interest includes filtering the mixture, spraying drying the mixture, or other steps for isolating a compound of interest.

In some embodiments, NaDES is used as an extraction solvent for processing botanical materials, such as leaves, including yerba mate leaves. As described throughout this disclosure, NaDES is an ideal solvent for the extraction of bioactives from plants and/or plant materials. In some embodiments, NaDESs increase solubility of phenolic acids.

NaDESs are a greener alternative to organic solvents, and because of their design capabilities and tunable properties, they can be customized further for the extraction of desired components as well as for use in various sectors, such as nutraceutical, pharmaceutical, cosmetic and food industry.

Some embodiments provided herein relate to compositions that include NaDESs and bioactive compounds that were purified, extracted, or isolated from a plant and/or plant material using the NaDESs, using the methods described herein. In some embodiments, the compositions are formulated for pharmaceutical, cosmetic, or food uses.

As used herein, the term "composition" or "formulation" has its ordinary meaning in light of the specification, and refers to a combination of elements, components, or compositions presented together for a given purpose.

The pharmaceutical compositions of the present disclosure may include an effective amount of NaDESs and one or more bioactive compounds isolated, purified, or extracted from a plant and/or plant material in combination with a pharmaceutically acceptable carrier. The effective amount (and the manner of administration) will be determined on an individual basis and will be based on a consideration of the subject (size, age, general health), the severity of the condition being treated, the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the compounds and combinations of compounds described herein can be determined using in vitro tests, animal models, or other dose-response studies, as are known in the art.

The pharmaceutical compositions of the disclosure may be prepared, packaged, or sold in formulations suitable for intradermal, intravenous, subcutaneous, oral, rectal, vaginal, parenteral, intraperitoneal, topical, pulmonary, intranasal, buccal, ophthalmic, intrathecal, epidural, or another route of administration. The compounds may be administered by any convenient route, for example by infusion or bolus injection, by absorption through epithelial or mucocutaneous linings (e.g., oral mucosa, rectal, and intestinal mucosa, etc.), and may be administered together with other biologically active agents. Administration can be systemic or local. Further, administration may be by a single dose or a series of doses.

The present disclosure thus also provides pharmaceutical compositions suitable for administration to a subject. The carrier can be a liquid, so that the composition is adapted for parenteral administration, or can be solid, a tablet or pill formulated for oral administration. Further, the carrier can be in the form of a nebulizable liquid or solid so that the composition is adapted for inhalation. When administered parenterally, the composition should be pyrogen free and in an acceptable parenteral carrier. Active compounds can alternatively be formulated or encapsulated in liposomes, using known methods. Other contemplated formulations include projected nanoparticles and immunologically based formulations.

Liposomes are completely closed lipid bilayer membranes that contain entrapped aqueous volume. Liposomes are vesicles that may be unilamellar (single membrane) or multilamellar (onion-like structures characterized by multiple membrane bilayers, each separated from the next by an aqueous layer). The bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase.

The compositions provided herein may further included suitable pharmaceutically acceptable carriers, stabilizers, diluents, buffers, or components for application, storage, bioavailability, solubility, or other component parts that improve the efficacy, aesthetics, or other properties of the compositions.

"Pharmaceutically acceptable" carriers are ones which are nontoxic to the cell or mammal being exposed thereto at the dosages and concentrations employed. Pharmaceutically acceptable carriers can be, but not limited to, organic or inorganic, solid or liquid excipients which is suitable for the selected mode of application such as topical, oral, or intravenous application, and administered in the form of a conventional pharmaceutical preparation, such as solid such as tablets, granules, powders, capsules, caplets, and liquid such as solution, spray, emulsion, foam, suspension, cream, lotion, ointment, salve, gel, and the like. Often the physiologically acceptable carrier is an aqueous pH buffered solution such as phosphate buffer or citrate buffer. The physiologically acceptable carrier may also include, for example, one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counter ions such as sodium, and nonionic surfactants such as Tween™, polyethylene glycol (PEG), and Pluronics™. Auxiliary, stabilizer, emulsifier, lubricant, binder, pH adjustor controller, isotonic agent, and other conventional additives may also be added to the carriers.

As described herein, the compositions including NaDESs and bioactive compounds from a plant and/or plant material can be formulated as a topical formulation. The topical formulation can further include, for example, a pharmaceutical vehicle that does not interfere with the function and viability of the NaDESs and bioactive compounds. The "pharmaceutical vehicle" as described herein refers to an inert substance with which a medication is mixed to facilitate measurement and administration of the topical formulation.

In some embodiments, the active ingredients and mixtures of active ingredients can be used, for example, in topical formulations including a pharmaceutically acceptable carrier prepared for storage and subsequent administration. As used herein, "topical" refers to the administration or application of a formulation to the skin or various body orifices. Some embodiments include use of compositions described herein in combination with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives and stabilizers can be provided in the topical formulation. Preservatives can be used to keep the nutrients for the skin cells from breaking down. As used herein, the terms "carrier or diluent" may be a solid carrier or diluent for solid formulations, a liquid carrier or diluent for liquid formulations, or mixtures thereof. Solid carriers/diluents include, but are not limited to, a gum, a starch (e.g., cornstarch, pregelatinized starch), a sugar (e.g., lactose, mannitol, sucrose, dextrose), a cellulosic material (e.g., microcrystalline cellulose), an acrylate (e.g., polymethyl acrylate), calcium carbonate, magnesium oxide, talc, or mixtures thereof. For liquid formulations, such as for topical or parenteral formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further include binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Topical formulations can be formulated and used as a solution, spray, emulsion, foam, suspension, cream, lotion, ointment, salve, or gel for topical application. Suitable ingredients in the topical formulation can include a for example, water, saline, dextrose, mannitol, lactose, lecithin, albumin, or sodium glutamate, and the like. If desired, absorption enhancing preparations (for example, liposomes), can be utilized. The topical formulations can further include, for example, one or more solvents, and/or at least one emollient.

As used herein, the term "injectable composition" refers to a formulation that is prepared for administration by injection. These injections may be administered by such routes as intravenous, subcutaneous, intradermal, intramuscular, intraarticular, or intrathecal.

In some embodiments, the pharmaceutical vehicle is soybean, grapefruit or almond oils, or synthetic fatty acid esters, such as ethyl oleate or triglycerides, or liposomes.

Coconut oil, olive oil, sesame oil, peanut oil, and soya can be used as suspension agents or lubricants in the topical formulation. In some embodiments, the topical formulations can include at least one thickener, at least one humectant, and/or at least one preservative. Thickeners can include, for example, triglycerides, palmitates, myristates, stearates, polyethylene glycol, vegetable-based fatty alcohols, copolymers, cellulose gum, or xanthan gum. Humectants can be used for their moisturizing capabilities. Without being limiting, humectants can include but are not limited to sodium PCA, nanolipid gels, glycerin, alpha-hydroxy acid, butylene glycol, propylene glycol, hexylene glycol, sorbitol, hyaluronic acid, urea, glyceryl triacetate, neoagarobiose, glycerol, xylitol, maltitol, polymeric polyols, polydextrose, quillaia, MP diol, seaweed and algae extracts, and lactic acid. In some embodiments, the topical formulation further includes at least one preservative. Without being limiting, preservatives can include benzoin resin, jojoba, vitamin E, alcohol, phenoxyethanol, methylparaben, propylparaben, diazolidinyl urea, sorbic acid, and triclosan. In some embodiments, the at least one preservative is benzoin resin, jojoba, vitamin E, alcohol, phenoxyethanol, methylparaben, propylparaben, diazolidinyl urea, sorbic acid, and/or triclosan.

The articles "a" and "an" are used herein to refer to one or to more than one (to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In certain embodiments, the "purity" of any given agent in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

Some embodiments relate to the following enumerated alternatives.

1. A method of isolating a plant extract from a plant material, the method comprising: obtaining a plant material; processing the plant material; mixing the processed plant material with a natural deep eutectic solvent (NaDES); and isolating a plant extract.

2. The method of alternative 1, wherein the plant material is obtained from yerba mate.

3. The method of any one of alternatives 1-2, wherein the NaDES comprises a hydrogen bond donor molecule and a hydrogen bond acceptor molecule.

4. The method of any one of alternatives 1-3, wherein the NaDES is sugar-based, organic acid-based, choline chloride-based, or polyol based.

5. The method of alternative 3, wherein the sugar-based NaDES is glucose, sucrose, fructose, or a combination thereof.

6. The method of alternative 3, wherein the organic acid-based NaDES is citric acid in combination with glucose, sucrose, fructose, or a combination thereof.

7. The method of alternative 3, wherein the choline chloride-based NaDES is choline chloride in combination with citric acid, glucose, sucrose, fructose, or a combination thereof.

8. The method of alternative 3, wherein the polyol-based NaDES is erythritol in combination with choline chloride, citric acid, glucose, fructose, sucrose, or a combination thereof.

9. The method of any one of alternatives 1-8, wherein the NaDES comprises choline chloride, citric acid, erythritol, glucose, sucrose, fructose, or a combination thereof.

10. The method of any one of alternatives 1-9, wherein the NaDES comprises choline chloride:citric acid, choline chloride:glucose, choline chloride:sucrose, choline chloride: fructose, glucose:sucrose, glucose:fructose, citric acid:glucose, citric acid:sucrose, citric acid:fructose, erythritol: choline chloride, erythritol:citric acid, or erythritol:glucose: fructose.

11. The method of any one of alternatives 1-10, wherein the NaDES comprises choline chloride and citric acid.

12. The method of alternative 11, wherein the choline chloride and citric acid are present in a ratio of 3:1.

13. The method of any one of alternatives 1-12, wherein the NaDES comprises water in an amount ranging from 10% to 80%.

14. The method of any one of alternatives 1-13, wherein the plant extract is a xanthine alkaloid, chlorogenic acid, or matesponin.

15. The method of alternative 14, wherein the xanthine alkaloid comprises caffeine, theobromine, theophylline, or an analogue or derivative thereof.

16. The method of alternative 14, wherein the chlorogenic acid comprises caffeic acid, tannin, or an analogue or derivative thereof.

17. The method of any one of alternatives 1-16, further comprising heating, stirring, centrifuging, and/or filtering following the mixing step.

18. The method of any one of alternatives 1-16, wherein the NaDES comprises choline chloride and citric acid present in a ratio of 3:1, and water present in an amount of 50%.

19. The method of alternative 10, wherein the NaDES are present in a mole ratio of 1:1.

20. The method of any one of alternatives 1-19, wherein the plant extract is theobromine, extracted in an amount ranging from about 5% to about 10% by weight.

21. A composition comprising: botanical isolates; and a natural deep eutectic solvent (NaDES).

22. The composition of alternative 21, wherein the botanical isolates comprise isolates from yerba mate.

23. The composition of any one of alternatives 21-22, wherein the botanical isolates comprise a xanthine alkaloid, chlorogenic acid, or matesponin.

24. The composition of any one of alternatives 21-23, wherein the botanical isolates comprise comprises caffeine, theobromine, theophylline, caffeic acid, tannin, or an analogue or derivative thereof.

25. The composition of any one of alternatives 21-24, wherein the NaDES comprises choline chloride, citric acid, erythritol, glucose, sucrose, fructose, or a combination thereof.

26. The composition of any one of alternatives 21-25, wherein the NaDES comprises choline chloride:citric acid, choline chloride:glucose, choline chloride:sucrose, choline chloride:fructose, glucose:sucrose, glucose:fructose, citric acid:glucose, citric acid:sucrose, citric acid:fructose, erythritol:choline chloride, erythritol:citric acid, or erythritol:glucose:fructose.

27. The composition of any one of alternatives 21-26, wherein the NaDES are present in a mole ratio of 1:1.

28. The composition of any one of alternatives 21-27, wherein the NaDES comprises choline chloride and citric acid.

29. The composition of alternative 28, wherein the choline chloride and citric acid are present in a ratio of 3:1.

30. The composition of alternative 21, comprising caffeine, theobromine, theophylline, caffeic acid, tannin, or an analogue or derivative thereof, choline chloride and citric acid present in a ratio of 3:1, and 50% water.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

The examples provided herein relate to methods of extracting, purifying, and isolating bioactive compounds from yerba mate using NaDESs. However, it should be understood that other plants and/or plant materials may be used using the methods, techniques, and assays described in the examples.

Materials and Methods

The experiments were conducted on powdered organic yerba mate leaves sourced from Triunfo. The chemicals, reagents and reference standards used for current research are list in Table 2.

TABLE 2

| Chemicals, Reagents and Reference standards | | |
|---|---|---|
| Name | Supplier | Lot NO |
| water | FISHER, HPLC GRADE | ZZLFS/W5-4 |
| methanol | FISHER, HPLC GRADE | ZZLFS/A452-4 |
| acetonitrile | FISHER, HPLC GRADE | ZZLFS/A998-4 |
| sodium hydroxide | Schedelco AR 99+% | ZZLSD/S0112-1 |
| hydrochloric acid | Honeywell 37%, | ZZLHW/10189005 |
| formic acid | Fisher, OPTIMA/CMS GRADE | ZZLFS/A117*50 |
| ethanol | FISHER, ABSOLUTE | ZZLFK/E/0650/17 |
| citric acid | FISHER, AR GRADE | ZZLFK/C/6200/60 |
| sucrose | FISHER | ZZLFK/S/8600/60 |
| D(+)-glucose | FISHER, ACS REAGENT | zzlac/41095-5000 |
| choline chloride | SIGMA, >98% | ZZLSM/C1879 |
| Folin-Ciocalteu phenol reagent | SIGMA, F9252 | BCCD8944 |
| aluminum chloride hexahydrate | SIGMA, 237078 | STBJ4732 |
| vanillin | Sigma, reagent PLUE, V1104 | BCCF3063 |
| sodium carbonate monohydrate | SIGMA, 99.5%, 230952 | MKCH8168 |
| chlorogenic acid | sigma C3878-250 mg | wxbd1890V |
| caffeine | sigma PHR1009-1G | LRAC4115 |
| theobromine | SIGMA, PHR1837-100 MG | LRAC5082 |
| rutin | SIGMA, PHL89570-50 MG | 66853802 |
| 3,5-dicaffeoylquinic acid | SIGMA, PHL80426-10 MG | 95324746 |
| 4,5-dicaffeoylquinic acid | SIGMA, PHL80427-10 MG | 111538786 |
| 3.4-docaffeoylquinic acid | sigma, PHL80425 | 113335440 |
| oleanolic acid | SIGMA, 1478141-15 MG | F05100 |
| ursolic acid | Sigma, 1707770-25 mg | F0L539 |
| ascorbic acid | Sigma, PHR1008-2G | LRAC2886 |
| DPPH | i-DNA Biotechnology, 14805-100 | 0590386-8 |

Preparation of Eutectic Solvent

The different components of the eutectic mixture (choline chloride, glucose, sucrose and citric acid) were weighed out and placed in the Erlenmeyer flask out of the specified order. Tap water, but preferably demineralized or distilled water, is then added at a concentration (by weight) that maintains physicochemical and microbiological integrity, said concentration being between 1 and 50%, preferably between 30 and 50%, and ideally, representing 50% by weight of the mixture. The eutectic mixture selected herein is citric acid to glucose (2:1, 1:1, 1:2 mol), citric acid to sucrose (2:1, 1:1, 1:2 mol) choline chloride to citric acid (1:1, 1:2, 1:3, 3:1, 2:1 mol), choline chloride to glucose (1:1 mol) choline chloride to sucrose (1:1 mol), each containing 30 wt % water; and choline chloride to citric acid (1:1 mol) containing 30%, 50%, and 80% water. However, it will be appreciated that other combinations of choline chloride and defined hydrogen bond donors may be used. The mixture was heated to 50° C.±2° C. and homogenized under magnetic stirring. Once the medium is completely dissolved and melted, it is placed at ambient temperature and then stored in a container until use.

Solid/Liquid Extraction by Maceration

Ten grams of yerba mate leaves powder was immersed in conventional solvent (water, water/citric acid, aqueous ethanol) or eutectic solvents. The mixture was heated in a 100 ml glass beaker under magnetic stirring. After extraction, liquid was transferred into the tube and centrifuged (3500 rpm for 10 min), then solid and liquid parts were separated by filtration using 5-7 μm cellulose filter paper.

Experimental Design:

The effects of three variables, extraction temperature (A), liquid/solid ratio (B), extraction time (C), were investigated and optimized using a three-level Box-Behnken Design (BBD). Therefore, a 15-run BBD, including three replicates at the center point, was used to fit a regression equation which was applied to optimize the process factors affecting extraction yield of yerba mate leaves. The factors and their levels are given in Table 3. For statistical calculations, the variables were coded +1, 0, and −1 for high, intermediate and low values, respectively.

TABLE 3

Independent factors and their levels used in study.

| | | Levels | | |
|---|---|---|---|---|
| Independent factor | Symbol | −1 | 0 | 1 |
| Temperature | A | 40 | 55 | 70 |
| Solvent/Feed ratio | B | 5 | 17.5 | 30 |
| Time | C | 60 | 120 | 180 |

Those factors and levels were considered significant to achieve optimum extraction conditions characterized by extraction yield and total chlorogenic acid (CGA) and caffeine content as dependent variables. The second-order polynomial model was used in the response surface analysis to predict the dependent variables and evaluate each extraction factor's effect. The model is explained by the Equation 1

$$Y = A_0 + \sum_{i=1} A_{ii} X_i^2 + \sum_{i=1j}^{n} \sum_{=i+1}^{n} A_{ij}\ X_i\ X_j \qquad \text{Equation 1}$$

where Y is the response variables, $A_0$, $A_i$, $A_{ii}$, and $A_{ij}$ are the regression coefficients for intercept, linear, quadratic and interaction terms, respectively; $X_i$ and $X_j$ represent the independent variables (i≠j). The models were used to evaluate the effect of each independent variable to the responses.

The experimental data analysis was performed using Design Expert Version 13 to yield regression equation and determine the optimum parameter combinations. The statistical significance of the model coefficients were determined by analysis of variance (ANOVA) combined with the application of Fisher's F-test at a probability P value of 0.05. The accuracy of the model was also checked by the coefficient of determination R2 as the measure of goodness of fit of the model. The fitted polynomial equation was then expressed in the form of three-dimensional response surfaces and two-dimensional contour plots to illustrate the relationship between the response and the variables.

Quantification of a Compound of Interest by High Performance Liquid Chromatography HPLC analyses were performed on the Thermo Fisher Vanquish series system equipped with a diode array detector (DAD) and Accucore C18 column (150 mm×2.1 mm, particle size 2.6 μm). Mobile phases for the separation were water/formic acid (99.9:0.1, v/v) (solvent A) and Acetonitrile/formic acid (99.9:0.1, v/v) (solvent B). The column temperature was kept at 30° C. and the autosampler at 4° C. The injection volume was 1 μl, the flow rate was set at 0.5 ml/min. Prior to analysis, samples were filtered through 0.22 μm PTFE (polytetrafluoroethylene) filters and analyzed with elution gradient indicated in Table 4.

TABLE 4

HPLC gradient program

| Time (min) | A (%) | B (%) |
|---|---|---|
| 0 | 95 | 5 |
| 10 | 80 | 20 |
| 12 | 80 | 20 |
| 15 | 95 | 5 |
| 15.1 | 5 | 95 |
| 16.5 | 5 | 95 |
| 16.6 | 95 | 5 |
| 19 | 95 | 5 |

The retention times and spectral data of yerba mate bioactives were compared with external standards. Caffeine and Theobromine were identified at 280 nm and chlorogenic acid (3-O-caffeoylquinic acid) (3-CQA), 4-O-caffeoylquinic acid (4-CQA), 5-O-caffeoylquinic acid (5-CQA), 3,4-dicaffeoylquinic acid (3,4-diCQA), 3,5-dicaffeoylquinic acid (3,5-diCQA), 4,5-dicaffeoylquinic acid (4,5-diCQA), and rutin were identified at 350 nm.

Each standard solution was prepared at concentration of 3 mg/ml in methanol and them mixed with the same volume to make the mixed solution at concentration of 0.5 mg/ml then stepwise diluted to 0.375, 0.25, 0.125, 0.025 and 0.005 mg/ml.

The concentration of each 3-CQA isomers were calculated as 3-CQA equivalent using an external standard method with calibration curves. The total CGA was calculated as the sum of the main CGA isomers, 3-CQA, 4-CQA, 5-CQA, 3,4-diCQA, 3,5-diCQA and 4,5-diCQA.

Testing the Physicochemical Efficacy as an Antioxidant 2,2-diphenyl-1-picrylhydrazyl (DPPH) is a free radical used to assess the free radical scavenging property of natural products. It is characterized as a stable free radical by the delocalization of the unpaired electron over the molecule as a whole, so the molecule does not dimerize, as would be the case with most other free radicals. The delocalization also gives rise to the deep violet color. When a DPPH solution is mixed with a compound that can donate a hydrogen atom, then this gives rise to the reduced form, diphenyl-picrylhydrazine, with loss of the violet color. The free radical scavenging activity of all the extracts was evaluated by 1,1-diphenyl-2-picryl-hydrazyl (DPPH) according to a previously reported method (Shen et al., 2010).

Thirty mg of dried extract of each sample was diluted in 10 ml of methanol, obtaining a concentration of 3 mg/mL as stock solution. From this stock solution were obtained the concentrations of 1.5, 0.75; 0.375; 0.1875; 0.09375; 0.046875; 0.0234275; and 0.01171825 mg/mL. Ascorbic acid, rutin, chlorogenic acid as pure reference standards were used as a positive control and dissolved in methanol to make the stock solution with the same concentration of extract solution.

DPPH (7.89 mg) was weighed on a chemical balance with a minimum weighing limit of 10 μg or smaller. Thereafter, it was dissolved in HPLC grade methanol to obtain a constant volume by filling 100 ml of a measuring flask (0.2 mM DPPH). Then further dilute this solution to 0.1 mM. The absorbance of a DPPH solution is empirically known to decrease with time until approximately 1 hr after preparation. Therefore, it was kept in dark for 2 hr until the absorbance stabilized.

The DPPH solution was stored in the dark at room temperature during the assay, and used up on the day of the preparation. 0.3 mL of each sample concentration and positive control was added to 2.7 mL of 0.1 mM DPPH solution. Reaction occurred inside tubes covered with aluminum paper, in a dark environment at 25° C. The mixtures were shaken vigorously and allowed to stand at room temperature for 30 minutes. Then the absorbance was measured at 517 nm using a microplate reader (Varioskan LUX, ThermoFisher). Control sample was prepared containing the same volume without any extract and reference ascorbic acid; methanol was used as blank and % scavenging of the DPPH free radical was measured using the following equation:

$$DPPH \text{ scavenging effect (\% inhibition)} = \{(Ac - As)/Ac\} * 100\}$$

Where, Ac=absorbance of DPPH alone, As=absorbance of DPPH along with different concentrations of extracts.

The measurements were done at eight points of concentration. The measurement for and analytical sample solution at each concentration was repeated three times.

The $IC_{50}$ of each analytical sample was calculated according to the following procedure: Inhibition ratio were plotted against the sample concentrations at all six points and the respective regression line (y=ax+b) was drawn. The regression line was not required to pass through the origin. In this step, we verified that all of the measurement points were on the regression line. In addition, it was also verified that two points at around 50% inhibition did not have a deviation from the regression line. When Y in the regression equation was substituted with 50, X (sample concentration) was calculated.

Example 1: Extraction of Bioactive Compounds from Yerba Mate

The following example demonstrates an embodiment of a method of extracting bioactive compound from yerba mate.

The extraction yields using NaDES were 2 times higher than those of conventional solvents, such as water and buffered water, indicating that NaDES displayed an obvious advantage for the extraction of bioactive compounds from yerba mate. Among the 20 kinds of NaDESs tested, the extraction yield of the target compound with the different types of NaDES differed. The organic acid-based NaDESs had higher extraction yields compared with those of the saccharide-based NaDESs. The presence of citric acid in NaDESs has a significant and unexpected impact. For example, for 5-CQA, the extraction yield increased 10 times. The extraction yield seems to be closely related to the properties of the solvents and the possible interaction between solutes and solvents. Therefore, the reasons for those results were the effect of hydrogen bonds formed between NaDESs and the target components. Meanwhile, among the NaDES containing citric acid, choline chloride and citric acid (CLCit) in the molar ratio of 3:1 exhibited the highest extraction yield. In addition, adding water and decreasing the viscosity of solvent have a noticeable impact on extraction yield. Therefore, CLCit3:1 with 50% water was selected as an advantageous NaDES for extracting bioactive components from yerba mate.

CLCit possess physicochemical characteristic desirable for extraction processes such as low pH value as well as polarity similar to polarity of water and polar organic solvents commonly used for extraction of polyphenolic compounds (ethanol and methanol) Extraction was performed by CLCit with 50% of water added, what leads to decreased viscosity of NaDES with water dilution, enhancement of the mass transfer from plant matrices to a solution, and consequent increase in the extraction efficiency. Furthermore, selected choline based NaDES having organic acid as a hydrogen bond donor is interesting due to biological activity of forming compounds itself (choline and citric acid) which probably could enhance biological activity of plant extracts as well.

Choline is an essential component of the human diet that is necessary for synthesis of acetylcholine, membrane and signaling phospholipid, and functions as an important methyl donor. A few studies observed positive association between the dietary choline intake or plasma concentration and risk of some types of cancer. The recommended daily requirement for choline is 550 mg/day, and 425 mg/day for non-pregnant women. The daily upper limit for adults is 3,500 mg/day which is the highest level of intake that is unlikely to cause harm. Similarly, citric acid also possesses various interesting biological activities, such as antioxidant, anti-inflammatory, and antitumor effects. Citric acid is found in large quantity in many fruits and vegetables, especially in citrus fruits, and is a common food and drink additive widely used by food industry as a chemical acidifier, flavoring agent, or a preservative. It is generally considered natural and healthy, and the Food and Drug Administration (FDA) does not pose limits for citric acid addition in food and drinks.

The extraction methods use heating and stirring, and is based on the solubilization of the target analytes in the deep eutectic solvent under heating and stirring conditions. The latter are optimized depending on the target compounds. Centrifugation and filtration steps can be used to separate the deep eutectic solvent phase from the sample solution. Synthesis of NaDES and extraction are achieved in one-pot, which make the process simple and scalable.

The synergy enhancement obtained by the solvent derives from a natural physicochemical phenomenon, which is called "eutectic formation", which is produced with the critical ratio of the mixture corresponding to the eutectic point is reached. The eutectic point is a point on the phase diagram that is located at the intersection of two liquid phase curves, resulting in a composition whose mixture is in the liquid phase at its lowest temperature.

In terms of extraction composition, the addition of water in a proportion by weight between 1 and 50%, preferably between 30 and 50%, in order to reduce the viscosity to a threshold compatible with industrial use.

The extraction methods described herein are carried out using a ternary mixture comprising water, choline chloride, and a hydrogen bond donor selected from polyols and organic acids, allows the critical eutectic formation of a molar ratio between choline chloride and hydrogen bond donor (ratio common for binary mixtures (choline chloride: hydrogen bond donor) and ternary mixtures (water; choline chloride: hydrogen bond donor)) to be maintained between 1:3 and 3:1. A surprising increase in the active species contained in the extract was obtained using this process. The process enables at least a 6-fold increase in active substance yield, such as 6, 7, 8, 9, 10, 11, 12, 13, 14, 15, 20, 25, or 30-fold yield increase.

The extraction method described herein include the following exemplary steps: the ground or unground yerba mate leaves immersed in the eutectic solvent were macerated, saturated and/or impregnated under atmospheric pressure, for example at 40 to 70° C. with agitation for 1 to 5 hours. The extraction phase did not involve any chemical transformation between any compounds present in the eutectic extraction solvent, which is completely inert with respect to the biological material and the natural substances to be extracted.

After optimization, choline chloride/citric acid at a 3:1 ratio was determined to possess high extraction efficiency for yerba mate. A response surface methodology (RSM) was used to optimize extraction conditions. Optimal conditions were: water concentration in NaDES was 50%; liquid/solid ratio 30; extraction temperature 55° C.; extraction time 180 min. The highest extraction yield was 78%. The content of bioactive compounds in optimized extracts were: caffeine, 23 mg/g; theobromine, 16 mg/g, rutin, 7 mg/g; total chlorogenic acids, 241 mg/g; chlorogenic acid, 55 mg/g; 4-CQA, 63 mg/g; 5-CQA, 35 mg/g; 3,4-diCQA, 12 mg/g; 3,5-diCQA, 54 mg/g; and 4,5-diCQA, 21 mg/g. Experimentally obtained values were in agreement with those predicted by RSM model, indicating suitability of the employed model and the success of RSM in optimizing the extraction conditions. Antioxidant properties characterized by DPPH inhibition $IC_{50}$ results exhibited remarkable higher antioxidant potential of antioxidants-loaded NaDES solution than the antioxidant in aqueous form. The sample with the best antioxidant activity ($IC_{50}$=64 μg $mL^{-1}$) was the one with choline chloride: citric acid (mol ratio 3:1) with 50% $H_2O$ addition (v/v). Comparing $IC_{50}$ of pure chlorogenic acid 258 μg/ml, the yerba mate extracts made by NaDES has four times greater antioxidant capability.

Example 2: Improved Extraction of Bioactive Components from Yerba Mate

The following example demonstrates an embodiment for improving the extraction of bioactive components from yerba mate.

Extraction of bioactive components from leaves of yerba mate was improved using the following three variables: the liquid ratio of yerba mate leaves to NaDES (from 5-30), extraction temperature (from 40-70° C.), and extraction time (from 1-3 hrs). Minitab software was used according to Box-Behnken design principle to obtain optimum yields, improved extraction efficiency, reduce energy consumption, and reduced the discharge of pollutant.

The effects of the three variables (extraction temperature, extraction time, and NaDES liquid to feed ratio) were investigated by using a three-level Box-Behnken Design (BBD). A 15-run BBD, including three replicates at the center point, was used to fit a regression equation which was applied to optimize the process factors affecting bioactives extraction yield and antioxidant properties. For statistical calculations, the variables were coded +1, 0, and −1 for high, intermediate and low values, respectively, as shown in Table 5.

TABLE 5

Box-Behnken Design (BBD) of independent variables and obtained data.

| | | | | | | | Yield (mg/g) | | | | | | | | | |
|---|---|---|---|---|---|---|---|---|---|---|---|---|---|---|---|---|
| A | B | C | Temp (° C.) | SF | Time (min) | Total Yield | Theobromine | caffeine | 4-CQA | 3-CQA | 5-CQA | Rutin | 3,4-DCQA | 4,5-DCQA | 3,5-DCQA | Total CQAs |
| 0 | −1 | 1 | 55 | 5 | 180 | 30.03 | 1.51 | 7.58 | 20.53 | 17.94 | 11.27 | 3.24 | 3.72 | 16.40 | 6.68 | 76.54 |
| 1 | 0 | 1 | 70 | 17.5 | 180 | 69.06 | 8.16 | 14.43 | 34.12 | 33.23 | 22.09 | 2.91 | 6.69 | 29.61 | 12.91 | 138.65 |
| 0 | 0 | 0 | 55 | 17.5 | 120 | 70.63 | 3.90 | 17.71 | 48.16 | 41.37 | 26.25 | 7.30 | 9.46 | 41.07 | 16.53 | 182.85 |
| 0 | 0 | 0 | 55 | 17.5 | 120 | 64.07 | 2.33 | 13.97 | 37.87 | 33.11 | 20.74 | 5.18 | 7.19 | 32.20 | 12.65 | 143.76 |
| 0 | −1 | −1 | 55 | 5 | 60 | 55.93 | 7.03 | 15.73 | 44.72 | 36.68 | 23.31 | 7.20 | 7.98 | 34.84 | 13.78 | 161.30 |
| −1 | −1 | 0 | 40 | 5 | 120 | 50.67 | 5.97 | 15.35 | 43.31 | 36.56 | 23.09 | 7.06 | 7.88 | 34.18 | 13.98 | 159.00 |
| −1 | 0 | −1 | 40 | 17.5 | 60 | 57.70 | 8.63 | 18.30 | 50.05 | 42.46 | 26.70 | 7.29 | 8.92 | 40.52 | 16.46 | 185.10 |
| 1 | 1 | 0 | 70 | 30 | 120 | 74.87 | 3.57 | 13.51 | 35.82 | 34.19 | 17.74 | 1.27 | 6.61 | 29.46 | 12.08 | 135.89 |
| 0 | 1 | 1 | 55 | 30 | 180 | 78.47 | 16.50 | 23.27 | 62.97 | 55.32 | 35.30 | 7.06 | 12.07 | 54.17 | 21.51 | 241.34 |
| 0 | 1 | −1 | 55 | 30 | 60 | 53.68 | 9.62 | 9.70 | 31.06 | 26.97 | 16.95 | 2.38 | 5.73 | 24.79 | 9.56 | 115.07 |
| 1 | 0 | −1 | 70 | 17.5 | 60 | 62.74 | 2.16 | 14.06 | 38.07 | 33.54 | 20.87 | 4.77 | 6.95 | 30.50 | 12.28 | 142.21 |
| 0 | 0 | 0 | 55 | 17.5 | 120 | 62.14 | 9.97 | 20.95 | 56.13 | 47.01 | 29.68 | 8.60 | 10.62 | 47.44 | 18.51 | 209.38 |
| −1 | 0 | 1 | 40 | 17.5 | 180 | 60.91 | 9.25 | 20.92 | 58.65 | 51.01 | 32.42 | 8.49 | 10.71 | 47.60 | 19.74 | 22.013 |
| 1 | −1 | 0 | 70 | 5 | 120 | 28.32 | 0.83 | 4.72 | 12.27 | 11.69 | 7.40 | 1.59 | 2.30 | 9.87 | 4.34 | 47.86 |
| −1 | 1 | 0 | 40 | 30 | 120 | 74.52 | 15.18 | 18.70 | 55.26 | 48.17 | 29.78 | 4.91 | 9.81 | 43.18 | 16.96 | 203.15 |

The experimental data analysis was performed using Minitab, to yield regression equation and determine the optimum parameter combinations. The statistical significance of the model coefficients were determined by analysis of variance (ANOVA) combined with the application of Fisher's F-test at a probability P value of 0.05. The accuracy of the model was also checked by the coefficient of determination R2 as the measure of goodness of fit of the model. The fitted polynomial equation was then expressed in the form of three-dimensional response surfaces and two-dimensional contour plots to illustrate the relationship between the response and the variables.

The optimal values of the independent parameters were obtained by solving the regression equation along with analyzing the response surfaces and contour plots. An additional experiment was subsequently conducted to verify the validity of the statistical experimental strategies.

Optimum conditions for the extraction process were intended to obtain maximum extraction yield as well as higher chlorogenic acid content. The optimal conditions were determined as follows: extraction temperature of 55° C., extraction time of 3 h, and NaDES solvent to feed ratio of 30. Triple validating experiments were conducted to confirm the prediction at a modified optimal condition in order to operate practically: The extraction yield and total chlorogenic acids content were 78% and 24% respectively, which were approximately equal to the predicted values by the regression models.

By multiple regression analysis on the experimental data, the predicted response for the extraction yield could be obtained via the second-order polynomial equation: Extraction yield (%)=0.621377+−0.0110222*A+0.145756*B+

0.0105304*C+0.0567341*AB+0.00778068*AC+0.126731*BC+0.0151577*A^2+−0.0655996*B^2+−0.0104967*C^2.

The F test and p-value were used to determine the significance of each coefficient. The high F value and small p-value mean significant corresponding variables. The Model F-value of 3.64 implies the model is not significant relative to the noise. There is a 15.80% chance that an F-value this large could occur due to noise. P-values less than 0.0500 indicate model terms are significant. In this case liquid/solid ratio is a significant model term. Values greater than 0.1000 indicate the model terms are not significant. Because there are many insignificant model terms (not counting those required to support hierarchy), model reduction to linear was used to improve. The reduced equation provided the following extraction yield, %=0.583877+−0.0110222*A+0.145756*B+0.0105304*C.

Figure 6A:
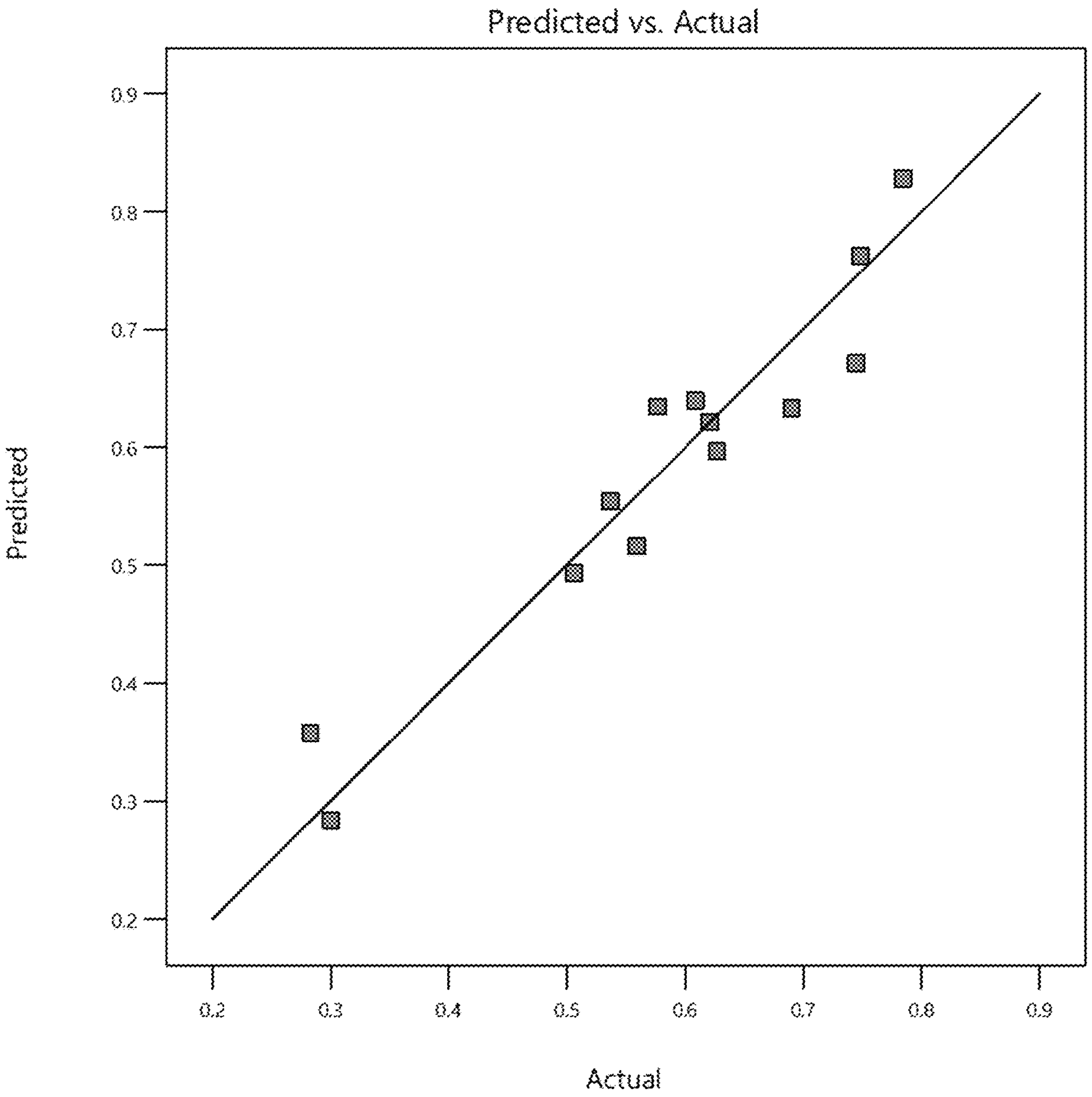
FIGS. 6A-6D depict graphs of response surface methodology (RSM) analysis.

The Model F-value of 4.42 implies the model is significant. The comparison of model predict value with actual value is shown in FIG. 6A. There is only a 3.60% chance that an F-value this large could occur due to noise. R2 value of 91.6% indicated that the form of the model represented the actual relationship was well correlated between the response and independent variables.

Figure 6B:
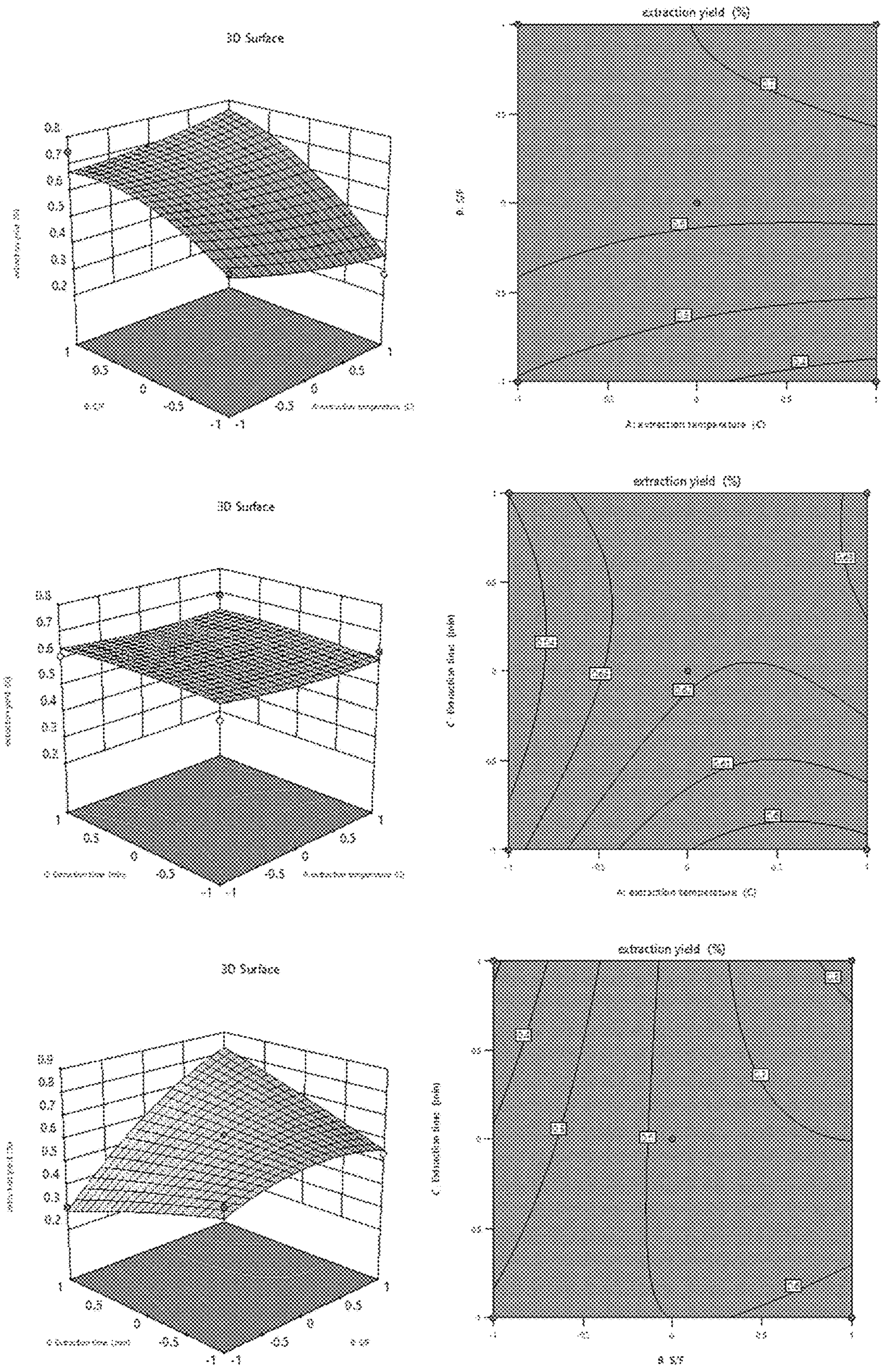

The three-dimensional response surfaces profiling multiple non-linear regression model was performed to depict the interactive effects of operational parameters. It provided a method to visualize the relationship between responses and experimental levels of each variable parameters and the type of interactions between two test variables. The results of extraction yield affected by extraction temperature, time, and solvent/feed ratio are shown in FIG. 6B. In the response surface and contour plots, extraction yield was obtained along with two continuous variables while the other one was fixed constant at its zero level (center value of the testing ranges). It was clear that extraction yield was sensitive to minor alterations of the test variables. Increasing extraction temperature leading to the increase of yield rapidly at first and then slowly indicated that higher extraction temperature was benefit to extraction to some extent. According to the regression coefficients significance of the quadratic polynomial model and gradient of slope in 3-D and contour plots, solvent/feed ratio was the most significant factor to affect extraction yield followed by extraction temperature and time. The highest extraction yield of 78% was achieve at middle extraction temperature of 55° C., the longest extraction time of 3 hrs and the highest liquid/solid ratio of 30.

The extraction methods were particularly attractive in that it exerts a synergistic/enhancing effect on the extraction process of yerba mate. The biological and/or physicochemical activities of the compounds contained in the extract were enhanced. The antioxidant activity induced by extraction with choline chloride-based eutectic solvents was 2-3 times higher than the extract produced by water.

In addition, since the eutectic solvent is edible and non-toxic, the corresponding extract can be directly formulated in foods and beverages (for human and animals), and cosmetics, nutraceuticals, cosmeceuticals, liquors, aromatics (spices and flavors), and pharmaceutical products in a finished product.

Example 3: Total Extraction Yield Results from Yerba Mate

The following example demonstrates an embodiment of extraction yield results of bioactive compounds from yerba mate.

Figure 5A:
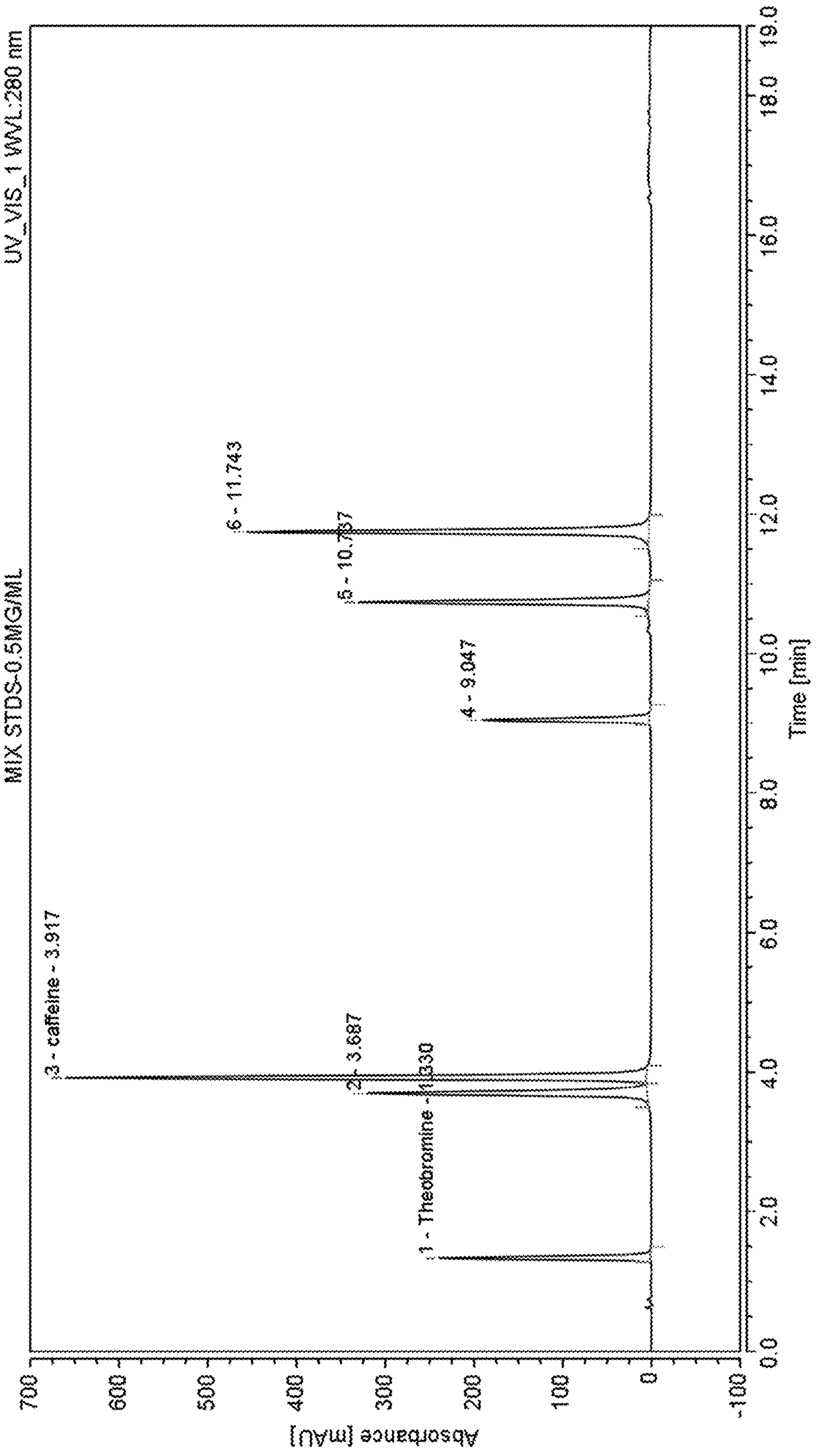
FIGS. 5A-5C depict chromatograms of mixed standards (FIGS. 5A and 5B) and one yerba mate extract sample (FIG. 5C).
Figure 5B:
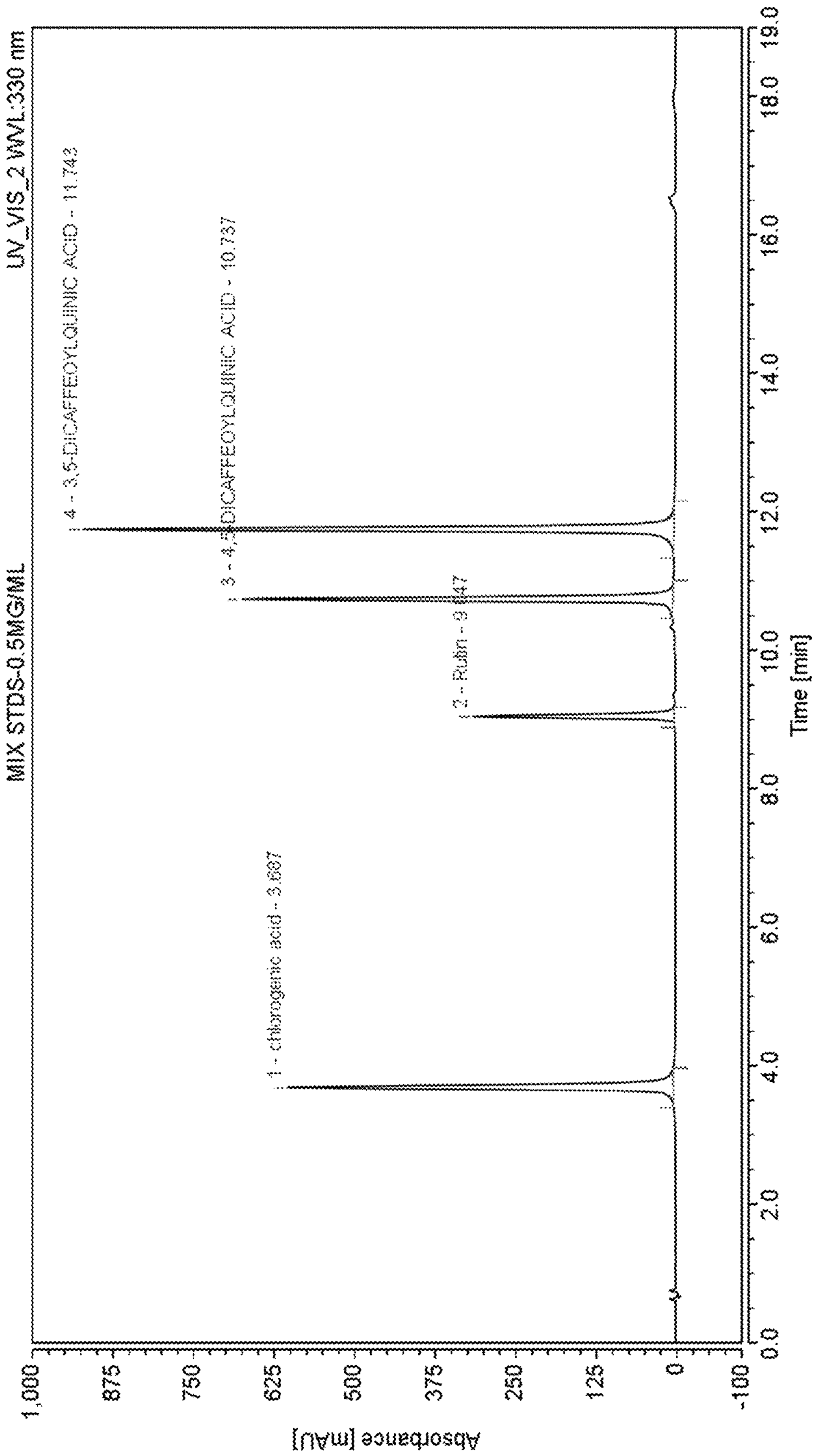
Figure 5C:
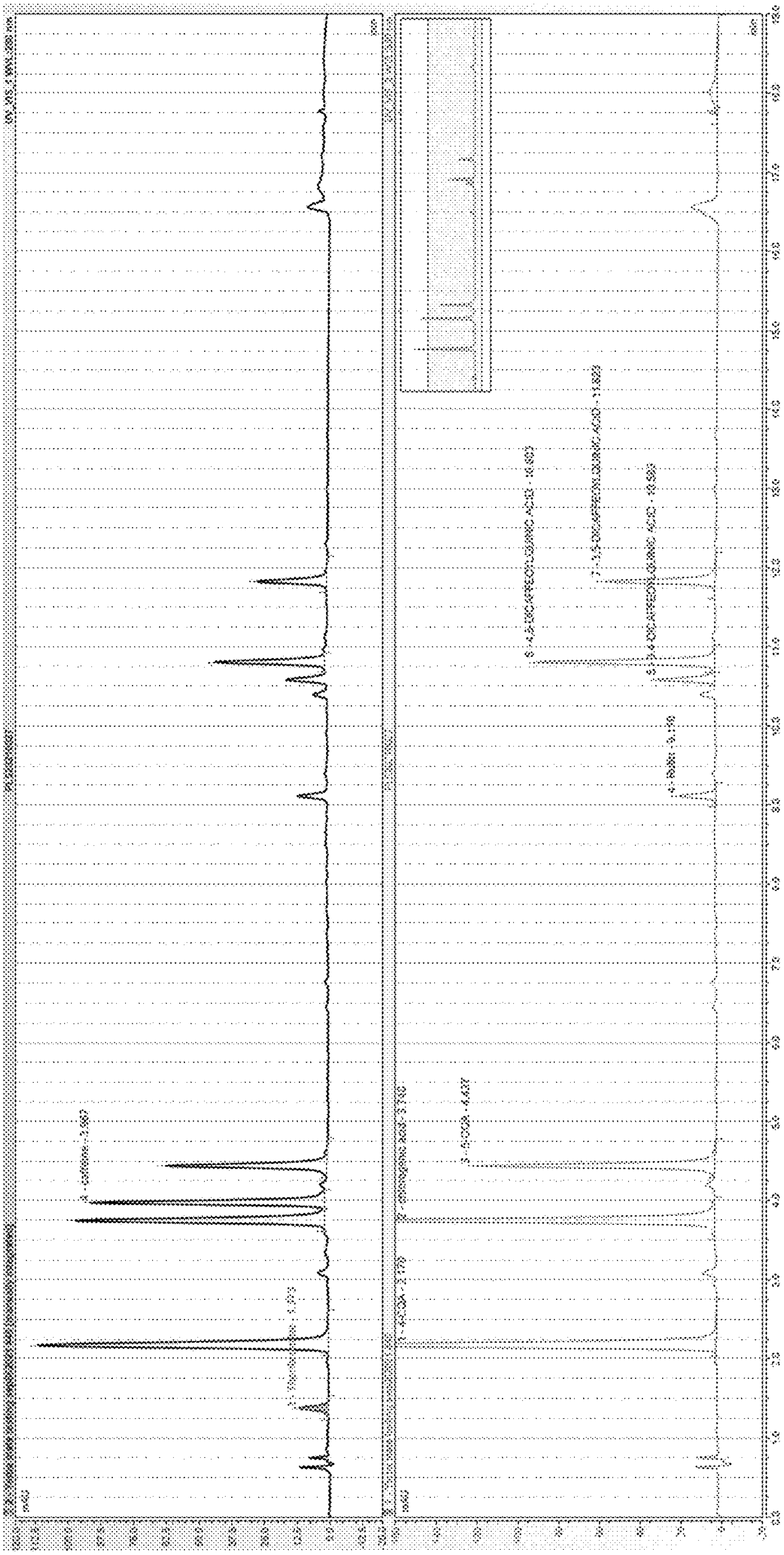

FIGS. 5A-5B show the chromatograms of mixed standards (FIGS. 5A and 5B) and one yerba mate extract sample (FIG. 5C). All major peaks were clearly separated and identified. The linearity was evaluated by building external calibration curves at concentration range of 5-500 ppm. The analyte peak area response was plotted versus its concentration at six different levels. From this, a coefficient of determination (R2) of greater than 0.993% for all analytes was achieved, demonstrating that the peak area response was linear and related to analytes concentration; enabling this approach to be used to quantitate bioactives in yerba mate processing.

When it comes to the extraction process of specific compounds from a plant material, the solvent choice is crucial. It is current belief that a solvent which solubilizes a compound would be a good phase for its extraction. Hence, a coarse screen to sift good extraction solvents from thousands of possibilities is usually to consider the following concepts: "like dissolves like" is a general principle (two molecules or solvents having similar polarity are soluble or miscible); solubility is higher when the temperature of the system increases; the higher the molecular weight of a solute, the lower its solubility in a given solvent; and extraction is predominantly determined by solubility phenomena.

Figure 2:
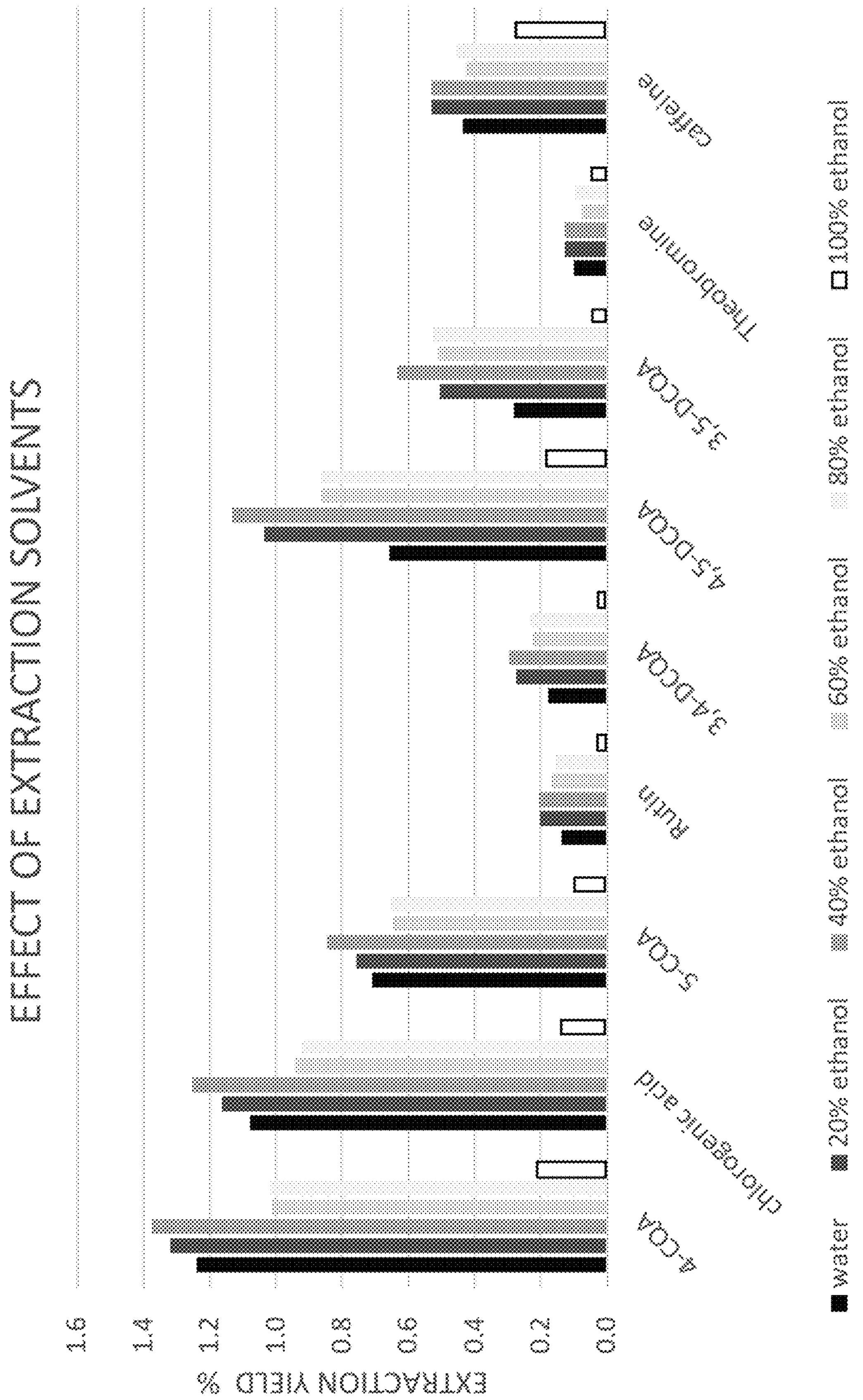
FIG. 2 depicts a bar graph showing extraction yield of conventional extraction solvents on yerba mate components. Typical extraction solvents include (from left to right): water; 20% ethanol; 40% ethanol; 60% ethanol; 80% ethanol; and 100% ethanol.

Yerba Mate leaves were extracted by conventional aqueous ethanol. The extraction yield, the purity of bioactives tested by HPLC and antioxidants $IC_{50}$ values are shown in Table 6 and FIG. 2.

TABLE 6

Yerba Mate Extraction Experiment Results by using different aqueous ethanol.

| | Extraction | Purity by HPLC (%) | | | | | | | | | | Yield of | $IC_{50}$ |
|---|---|---|---|---|---|---|---|---|---|---|---|---|---|
| Extraction Solvent | yield (%) | 4-CQA | chlorogenic | 5-CQA | Rutin | 3,4-DCQA | 4,5-DCQA | 3,5-DCQA | Theobromine | caffeine | TotalCQAs, % | CQAs (%) | (mg/ml) |
| Water | 20.08 | 6.18 | 5.37 | 3.53 | 0.68 | 0.88 | 3.28 | 1.40 | 0.50 | 2.18 | 20.65 | 4.82 | 510 |
| 20% ethanol | 15.90 | 8.31 | 7.32 | 4.76 | 1.27 | 1.73 | 6.52 | 3.18 | 0.80 | 3.34 | 31.82 | 5.92 | 322 |
| 40% ethanol | 22.41 | 6.14 | 5.59 | 3.78 | 0.93 | 1.33 | 5.06 | 2.83 | 0.57 | 2.37 | 24.37 | 6.41 | 495 |
| 60% ethanol | 17.65 | 5.75 | 5.35 | 3.67 | 0.95 | 1.29 | 4.90 | 2.89 | 0.42 | 2.41 | 23.86 | 4.88 | 437 |
| 80% ethanol | 22.25 | 4.58 | 4.16 | 2.95 | 0.71 | 1.05 | 3.89 | 2.37 | 0.45 | 2.06 | 19.00 | 4.94 | 590 |
| 100% | 17.20 | 1.23 | 0.82 | 0.59 | 0.16 | 0.19 | 1.07 | 0.26 | 0.29 | 1.58 | 4.16 | 1.07 | 1970 |

TABLE 6-continued

| Yerba Mate Extraction Experiment Results by using different aqueous ethanol. | | | | | | | | | | | | | |
|---|---|---|---|---|---|---|---|---|---|---|---|---|---|
| | Extraction | Purity by HPLC (%) | | | | | | | | | | Yield of | $IC_{50}$ |
| Extraction Solvent | yield (%) | 4-CQA | chlorogenic | 5-CQA | Rutin | 3,4-DCQA | 4,5-DCQA | 3,5-DCQA | Theobromine | caffeine | TotalCQAs, % | CQAs (%) | (mg/ml) |
| ethanol | | | | | | | | | | | | | |

The results of phytochemical screening of the ethanol extracts of yerba mate leaves showed the presence of alkaloids, phenolics, and flavonoids. Although the ethanol used for extraction was in different concentrations, it was still able to attract the same type of compound class from the yerba mate leaves. The choice of ethanol as the extraction solvent was considered to provide many advantages over other organic solvents, which is relatively safer (less toxic). Ethanol has the ability to attract glycosides, polyacetylenes, sterols, polyphenols, tannins, flavonols, terpenoids, and alkaloids. Ethanol is a protic organic solvent with a polarity index value of 5.2 and a dielectric constant of 24.55. The polarity of ethanol in the six concentrations used in this example was influenced by concentration of water contained in mixed solvents. The more water, the higher its polarity compared to absolute ethanol. Solvents with high polarity had the ability to extract a class of compounds with a wider polarity. This allowed non-phenolic polar compounds such as carbohydrates and proteins to be dissolved during the extraction process which resulted in increased extraction yields. The 40% ethanol in this study was able to extract more metabolites than other ethanol solvents.

Figure 3:
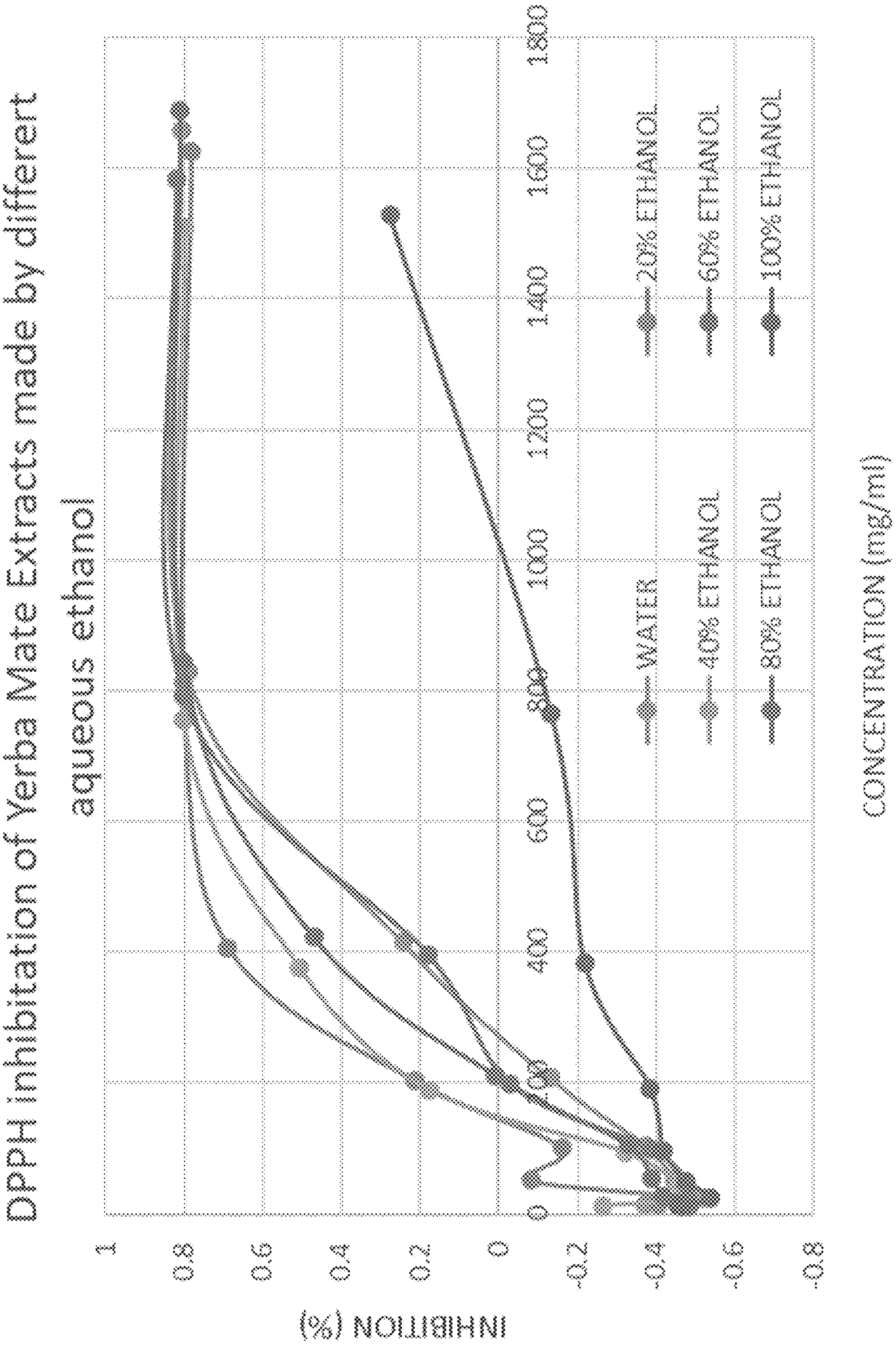
FIG. 3 depicts a line graph showing antioxidant assay results of yerba mate extracts in different solvents using 2,2-diphenyl-1-picrylhydrazyl (DPPH) radicals.

Antioxidant activity testing in this study was carried out using DPPH radicals. This method is considered relatively inexpensive, effective, and efficient and has good sensitivity using UV-Vis spectrophotometry. DPPH is a free radical with a dark blue color. With the presence of an antioxidant, the antioxidant donates its hydrogen atom to the DPPH radical (becoming a DPPH-H). This reaction is characterized by a decrease in absorbance due to DPPH loses its reactivity. The antioxidant activity in this study was determined based on the $IC_{50}$ value of the sample, as shown in FIG. 3. The $IC_{50}$ value showed the sample concentration needed to inhibit 50% of DPPH radicals. This value was obtained from the results of calculations using linear regression analysis. The smaller the $IC_{50}$ value of an antioxidant, the higher its power to inhibit free radicals. Based on the results summarized in Table 6, the 20% ethanol extract of yerba mate leaves had the highest antioxidant activity with an $IC_{50}$ value of 322 mg/ml. This showed that the 20% ethanol extract of yerba mate leaves had a strong DPPH radical scavenging activity. The antioxidant property of extract is highly correlated with total chlorogenic acid (total CQAs) with or without caffeine. As expected, caffeine has no contribution to extract's antioxidant property.

One of the critical properties of an aqueous extraction medium is its pH. Because extractables normally are acidic or basic compounds, the pH of the extraction solvent is a critical extraction design parameter, as the solubility, of an acidic or basic leachable (or extractable) will be pH-dependent. In this experiment, sodium citrate was used to adjust the PH of water solution, and the effect of pH on the extraction efficiencies within the range of 2-5 were investigated and the results are shown in Table 7.

TABLE 7

| Effect of pH on extraction efficacy of yerba mate leaves | | | | | | | | | | | | |
|---|---|---|---|---|---|---|---|---|---|---|---|---|
| | Extraction | Purity by HPLC (%) | | | | | | | | | | $IC_{50}$ |
| pH | yield (%) | 4-CQA | 3-CQA | 5-CQA | Rutin | 3,4-DCQA | 4,5-DCQA | 3,5-DCQA | Theobromine | caffeine | TotalCQAs, % | (mg/ml) |
| 2 | 60.90 | 2.56 | 2.18 | 1.41 | 0.31 | 0.30 | 1.00 | 0.38 | 0.16 | 0.97 | 7.82 | 727.07 |
| 2.32 | 28.45 | 5.20 | 4.71 | 3.10 | 0.63 | 0.57 | 1.80 | 0.69 | 0.49 | 2.01 | 16.06 | 375.19 |
| 2.71 | 21.43 | 5.71 | 5.32 | 3.50 | 0.67 | 0.70 | 2.24 | 0.90 | 0.49 | 2.18 | 18.37 | 290.38 |
| 2.92 | 43.71 | 3.18 | 3.00 | 1.93 | 0.36 | 0.48 | 1.69 | 0.68 | 0.27 | 1.22 | 10.96 | 486.24 |
| 3.42 | 47.55 | 3.10 | 2.71 | 1.76 | 0.36 | 0.37 | 1.18 | 0.47 | 0.20 | 1.16 | 9.58 | 636.75 |
| 4.56 | 48.02 | 3.68 | 3.28 | 2.13 | 0.43 | 0.56 | 1.96 | 0.82 | 0.22 | 1.36 | 12.43 | 311.32 |
| 4.95 | 58.96 | 2.79 | 2.67 | 1.74 | 0.34 | 0.43 | 1.57 | 0.65 | 0.26 | 1.10 | 9.85 | 416.50 |
| water | 20.08 | 6.18 | 5.37 | 3.53 | 0.68 | 0.88 | 3.28 | 1.40 | 0.50 | 2.18 | 20.65 | 610 |

Total extraction yield was increased significantly by lower pH. Under strongly acidic conditions, the effect of pH on yerba mate leaves extraction yield may be attributed to the action of $H^+$ on leaves, altering leaves structure in such a way that some extra solids are liberated. $H^+$ might open parts of the leaf structure that are usually inaccessible and had more water soluble components released from the leaves. On the other hand, some insoluble substances, such as polysaccharides, pectin, and/or protein, may be hydrolyzed during extraction under strongly acidic conditions. Maximum solids extracted from yerba mate with hot water was about 200 g/kg, while about 600 g solids per kg of dry leaves were extracted at pH 2. This suggested that about 400 g more solids per kg yerba mate was released by the action of $H^+$.

Compared to water, lower pH also increases recovery rate of bioactives. The recovery rate of chlorogenic acid by water was 62.29%, by lower pH to 4.56, the recovery rate was 91.12%. As discussed previously, DPPH antioxidant property are directly related with the content of chlorogenic acids. Lower pH to 4-5, also decreased $IC_{50}$ values and improved antioxidants. Compared with aqueous ethanol, water/citric acid is a better extraction solvent for yerba mate leaves.

The component of NaDES has significant influence on its physicochemical properties such as polarity, viscosity, and solubilization ability. NaDESs directly affect the extraction efficiency of target compounds. In order to select a suitable NaDES, 20 different types of NaDES were prepared by four kinds of primary metabolites, and their extraction yields of bioactives from yerba mate leaves were tested by HPLC. The extraction temperature and time were 50° C. and 120 min, and the extraction solvent used was NaDES with the addition of 0, 30, 50, and 80% (w/w) water because of their high viscosity, which could lower the mass transport efficiency. Water and water/citric acid (buffered water) were used as comparison, with results shown in Table 8 and FIG. 4.

the ratio change of chlorine chloride (Cl)/citric acid (Cit) ratio from 1:3 to 3:1 enhanced the extraction yield of chlorogenic acids. This may be because the number of the hydrogen bonds changed, thus contributing to the breakage of plant cell wall and the dissolution of target components. Therefore, the combination of choline chloride/citric acid with a mole ratio of 3:1 was used for further examples.

As well as the molar ratio of solvent components, the different water content of the NaDESs could also affect the viscosity of the solvents, leading to differences in extraction yield. Therefore, the extraction yields of NaDESs with water content ranging from 0% to 80% were researched. The results showed that the extraction process was improved as the water content in NaDESs increased from 0% to 80%. This is because of the significant reduction in solvent viscosity and surface tension caused by adding water which would help with the process of mass transfer from materials to solvents. Water plays an important role in the properties and structure of NaDESs. Water can lead to a reduction in density and viscosity and increase in polarity. According to previous studies, the supramolecular complex of NaDES is preserved if the volume of added water is less than 50%. Above this percentage, the H-bonds between hydrogen bond acceptor and hydrogen bond donor could be weakened gradually by excessive addition of water, and the resulting mixture may consist merely of dissociated NaDES compounds. Therefore, a water content of 50% was used for further studies.

TABLE 8

Extraction yield of yerba mate by different NaDESs

| NaDES | Extraction yield (%) | 4-CQA | 3-CQA | 5-CQA | Rutin | 3,4-DCQA | 4,5-DCQA | 3,5-DCQA | Theobromine | caffeine | Total CQAs % |
|---|---|---|---|---|---|---|---|---|---|---|---|
| clglu1:1, 30% | 74.20 | 1.39 | 1.18 | 0.12 | 0.75 | 0.24 | 1.03 | 0.40 | 0.12 | 0.51 | 4.36 |
| clsuc1:1, 30% | 49.94 | 1.69 | 1.35 | 0.09 | 0.22 | 0.27 | 1.17 | 0.45 | 0.15 | 0.59 | 5.02 |
| citglu1:1, 30% | 53.36 | 1.43 | 1.20 | 0.09 | 0.17 | 0.22 | 0.92 | 0.35 | 0.10 | 0.56 | 4.22 |
| citsuc1:1, 30% | 53.72 | 1.38 | 1.12 | 0.09 | 0.15 | 0.20 | 0.83 | 0.31 | 0.07 | 0.53 | 3.93 |
| clcitglu1:1:1, 30% | 49.64 | 1.71 | 1.42 | 0.09 | 0.24 | 0.29 | 1.27 | 0.50 | 0.16 | 0.67 | 5.28 |
| clcitsuc1:1:1, 30% | 59.53 | 1.47 | 1.22 | 0.10 | 0.17 | 0.23 | 0.97 | 0.37 | 0.15 | 0.54 | 4.36 |
| clcit3:1, 30% | 68.76 | 2.68 | 2.23 | 1.44 | 0.42 | 0.52 | 2.23 | 0.95 | 0.24 | 0.94 | 10.05 |
| clcit2:1, 30% | 77.26 | 1.98 | 1.68 | 1.08 | 0.27 | 0.37 | 1.58 | 0.68 | 0.13 | 0.69 | 7.38 |
| clcit1:1, 30% | 73.20 | 2.01 | 1.73 | 1.10 | 0.29 | 0.38 | 1.61 | 0.69 | 0.14 | 0.76 | 7.52 |
| clcit1:2, 30% | 67.51 | 2.15 | 1.87 | 1.19 | 0.31 | 0.40 | 1.68 | 0.73 | 0.21 | 0.87 | 8.02 |
| clcit1:3, 30% | 60.49 | 2.03 | 1.73 | 1.12 | 0.31 | 0.38 | 1.58 | 0.69 | 0.14 | 0.80 | 7.52 |
| clcit1:1, 50% | 50.85 | 2.12 | 1.79 | 1.15 | 0.32 | 0.38 | 1.62 | 0.67 | 0.15 | 0.80 | 7.73 |
| clcit1:1, 80% | 56.36 | 2.56 | 2.12 | 1.37 | 0.40 | 0.36 | 1.41 | 0.56 | 0.25 | 0.96 | 8.38 |
| water | 20.08 | 1.24 | 1.08 | 0.71 | 0.14 | 0.18 | 0.66 | 0.28 | 0.10 | 0.44 | 4.15 |
| buffered water | 48.02 | 2.16 | 1.93 | 1.25 | 0.25 | 0.33 | 1.15 | 0.49 | 0.12 | 0.79 | 7.30 |

CL is choline chloride; CIT is citric acid; GLU is glucose; SUC is sucrose.

Figure 4:
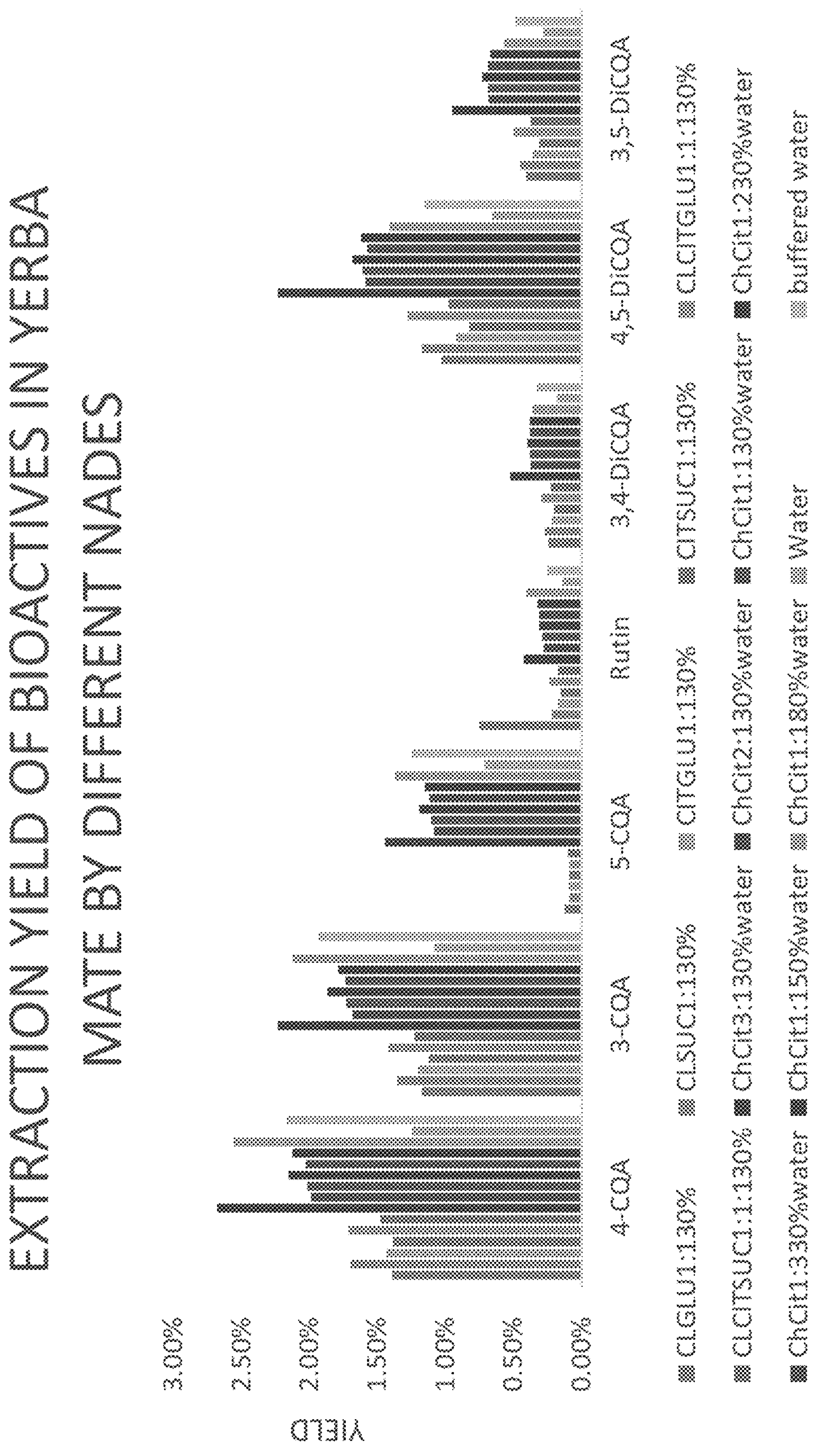
FIG. 4 depicts a bar graph showing extraction yield of bioactive compounds from yerba mate by different NaDESs, including (from left to right): CLCIT1:1, 30% water; CLGLU1:1, 30% water; CLSUC1:1, 30% water; CITGLU1:1, 30% water; CITSUC1:1, 30% water; CLCITGLU1:1:1, 30% water; CLCITSUC1:1:1, 30% water; CLCIT3:1, 30% water; CLCIT2:1, 30% water; CLCIT1:2, 30% water; CLCIT1:3, 30% water; CLCIT1:1, 50% water; CLCIT1:1, 80% water; water; and buffered water. CL is choline chloride; CIT is citric acid; GLU is glucose; and SUC is sucrose.

As shown in Table 8 and FIG. 4, the extraction yields of NaDESs were 3 times higher than water, indicating that NaDES displayed a surprising and unexpected advantage for the extraction of yerba mate. Among the 20 kinds of NaDESs, the extraction yield of the target compound with the different type of NaDES differed. The organic acids-based NaDESs had higher extraction yield compared with those of saccharide-based NaDESs, which indicated that the existence of organic acid benefits the increase of extraction yield. As expected, the extraction yield is closely related to the properties of the solvents and the possible interaction between solutes and solvents. The reasons for higher extraction yield was the effect of hydrogen bonds formed between NaDESs and the target components.

The data also reveals the influence of the different NaDESs ratios on the extraction yield. The results show that Considering the principles of green extraction with NaDESs, choline chloride (Cl)/citric acid (Cit) were chosen as optimized NaDESs for extraction yerba mate leaves. ClCit possesses physicochemical characteristic desirable for extraction processes such as low pH value as well as polarity similar to polarity of water and polar organic solvents commonly used for extraction of polyphenolic compounds (ethanol and methanol). Extraction was performed by ClCit with 50% of water added, what leads to decreased viscosity of NaDES with water dilution, enhancement of the mass transfer from plant matrices to a solution and consequently increase in the extraction efficiency. Furthermore, selected choline based NaDES having organic acid as hydrogen bond donor is interesting due to biological activity of forming compounds itself (choline and citric acid) which probably could enhance biological activity of plant extracts as well.

Example 4: Bioactive Compounds in Yerba Mate

The following example demonstrates extraction parameters for various yerba mate bioactive compounds.

Box-Behnken design (BBD) combined with response surface methodology (RSM) was used to optimize the extraction conditions of total chlorogenic acid (Total CQA), chlorogenic acid, 4-caffeoylquinic acid (4-CQA), 5-o-caffeoylquinic acid (5-CQA), 3,4-dicaffeoylquinic acid (3,4-diCQA), 3,5-dicaffeoylquinic acid (3,5-diCQA), 4,5-dicaffeoylquinic acid (4,5-diCQA), rutin, theobromine, and caffeine.

Total CQA

The yield of total chlorogenic acid (Y1) was function of these variables. Extraction temperature (A), liquid/solid ratio (B), and extraction time (C) were independent variables. By applying multiple regression analysis to the experimental data, the following second order polynomial equations were found to represent the extraction yield of total chlorogenic acids: Y1=209.381+−37.8462*A+31.3421*B+9.12204*C+10.9688*AB+−9.64654*AC+52.7593*BC+−24.9719*A^2+−47.9325*B^2+−12.8844*C^2.

Figure 6C:
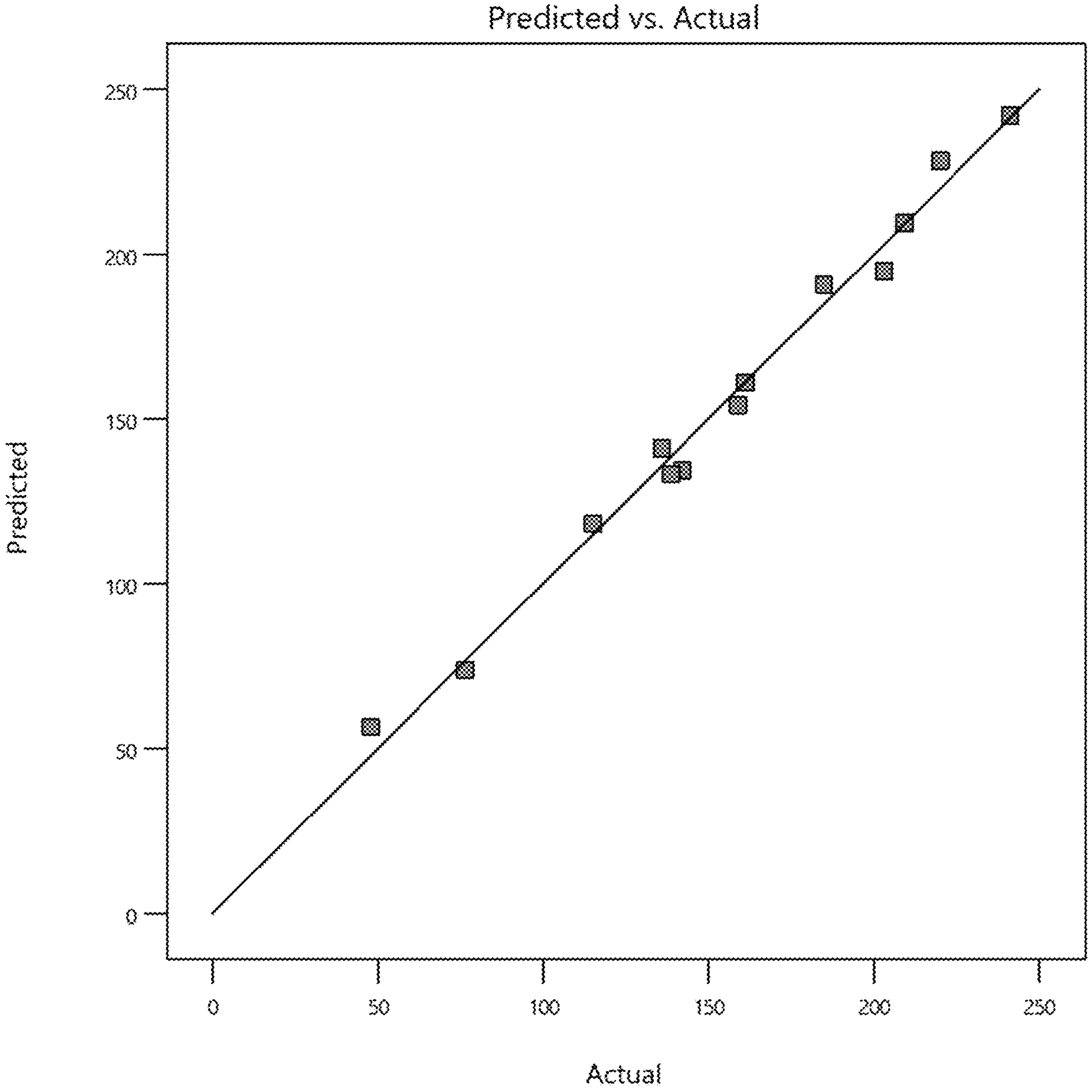

For total chlorogenic acids, the Model F-value of 31.21 and associated P value less than 0.05 indicated that the regression model is significant. There is only a 0.82% chance that an F-value this large could occur due to noise. P-values less than 0.0500 indicate model terms are significant. In this case A, B, BC, $A^2$, $B^2$ are significant model terms. The high value of R2 (0.9894) and adj-R2 (0.9577) indicated that the form of the model represented the actual relationship was well correlated between the response and independent variables. At the same time, a low value (7.38) of coefficient of the variation (CV) clearly indicated a high precision and a good reliability of the experimental values. The comparison of model predict value with actual value is shown in FIG. 6C.

Figure 6D:
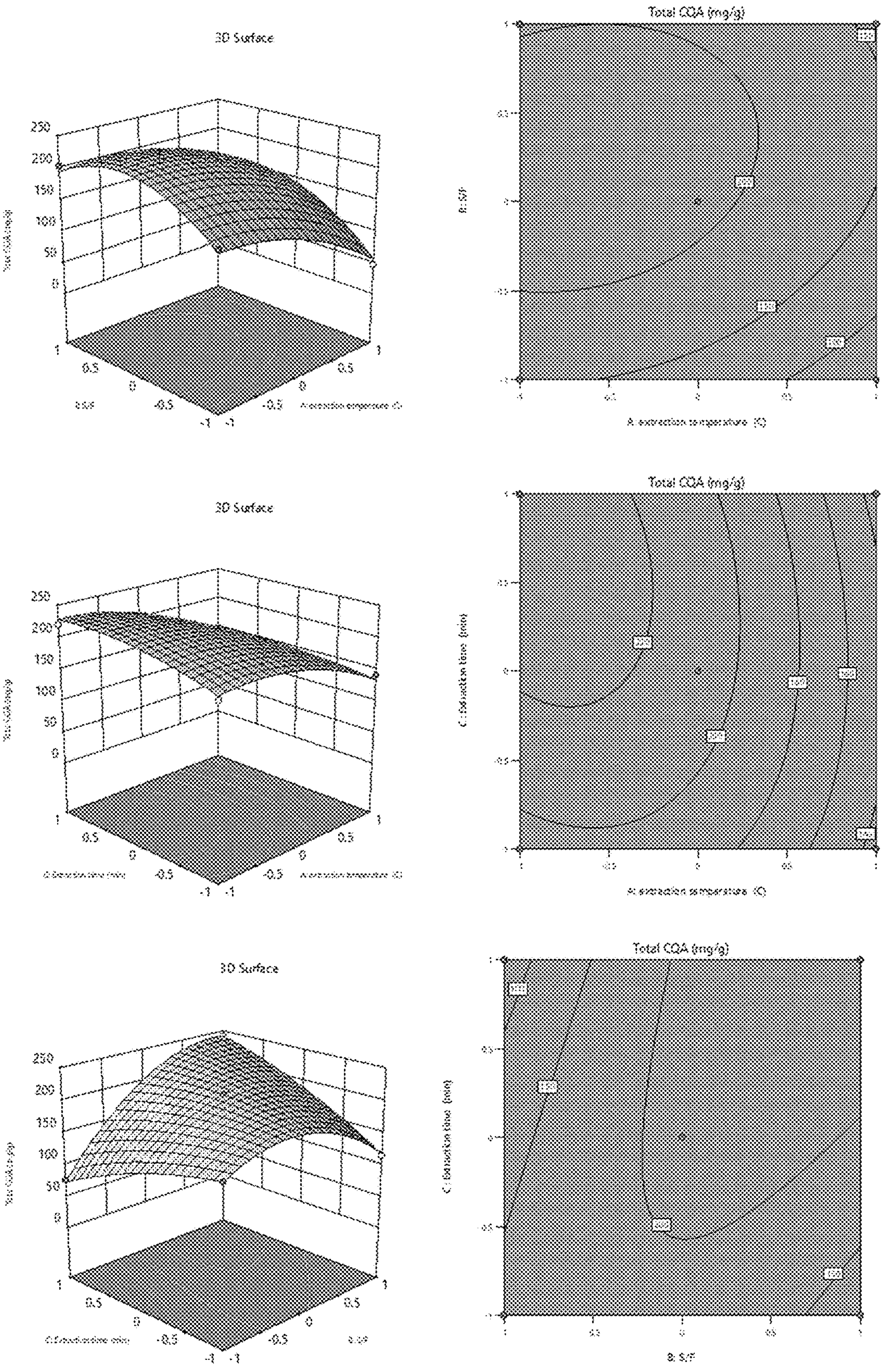

The three-dimensional (3-D) response surface and contour plots were the graphical representations of the regression. It provided a method to visualize the relationship between responses and experimental levels of each variable parameters and the type of interactions between two test variables. The results of extraction yield affected by extraction temperature, liquid/solid ratio, and time are shown in FIG. 6D. Table 9 shows coefficients calculated from regression model according to ANOVA.

TABLE 9

ANOVA statistics of quadratic model for the extraction yields of total chlorogenic acid.

| Source | Sum of Squares | df | Mean Square | F-value | p-value |
|---|---|---|---|---|---|
| Model | 37525.55 | 9 | 4169.51 | 31.21 | 0.0082 |
| A-extraction temperature | 11458.67 | 1 | 11458.67 | 85.78 | 0.0027 |
| B-S/F | 7858.60 | 1 | 7858.60 | 58.83 | 0.0046 |
| C-extraction time | 665.69 | 1 | 665.69 | 4.98 | 0.1118 |
| AB | 481.26 | 1 | 481.26 | 3.60 | 0.1539 |
| AC | 372.22 | 1 | 372.22 | 2.79 | 0.1937 |
| BC | 11134.17 | 1 | 11134.17 | 83.35 | 0.0028 |
| $A^2$ | 1425.36 | 1 | 1425.36 | 10.67 | 0.0469 |
| $B^2$ | 5251.49 | 1 | 5251.49 | 39.31 | 0.0082 |
| $C^2$ | 379.45 | 1 | 379.45 | 2.84 | 0.1905 |
| Residual | 400.74 | 3 | 133.58 | | |
| Cor Total | 37926.30 | 12 | | | |

In the response surface and contour plots, total chlorogenic acids extraction yield was obtained along with two continuous variables while the other one was fixed constant at its zero level (center value of the testing ranges). From the sharpness of the response surface, the interaction was significant. When liquid/solid kept at optimum level, the extraction yield of total chlorogenic acids increased with increase temperature. However, when temperature got over a certain value, the extraction yield decreased, due to high temperature that decomposes active compounds. It showed that the active compounds could also decompose during a long time extraction. The liquid/solid ratio affected the extraction yield significantly. As the solid/liquid ratio increased from 5 to 30, the percentage yield increased from 76 mg/g to 241 mg/g. The maximum value of 241 mg/g total chlorogenic acid was obtained when the liquid/solid ratio, temperature, and extraction time were respectively controlled to be 30 g/g, 55° C. and 180 min.

Chlorogenic Acid

By applying multiple regression analysis to the experimental data, the following second order polynomial equations were found to represent the extraction yield of chlorogenic acids (Y2): Y2=47.0091+−8.19396*A+7.72104*B+2.22975*C+2.71997*AB+−2.21339*AC+11.771*BC+−4.26374*A^2+−10.0948*B^2+−2.68677*C^2.

For chlorogenic acids, the Model F-value of 26.57 and associated P value less than 0.05 indicated that the regression model is significant. There is only a 1.04% chance that an F-value this large could occur due to noise. P-values less than 0.0500 indicate model terms are significant. In this case A, B, BC, B2 are significant model terms. The high value of R2 (0.9876) and adj-R2 (0.9504) indicated that the form of the model represented the actual relationship was well correlated between the response and independent variables. At the same time, a low value (7.71) of coefficient of the variation (CV) clearly indicated a high precision and a good reliability of the experimental values.

The three-dimensional (3-D) response surface and contour plots were the graphical representations of regression. It provided a method to visualize the relationship between responses and experimental levels of each variable parameters and the type of interactions between two test variables. In the response surface and contour plots, chlorogenic acid extraction yield was obtained along with two continuous variables while the other one was fixed constant at its zero level (center value of the testing ranges).

From the sharp of the response surface, the interaction was significant. When liquid/solid kept at optimum level, the extraction yield of chlorogenic acids increased with increase temperature. However, when temperature got over a certain value, the extraction yield decreased. It was because that high temperature could make chlorogenic acid decomposed. It showed that the at lower extraction temperatures, the extraction yield increase with increasing liquid/solid ratio. Both extraction time and the liquid/solid ratio affected the extraction yield significantly. As the solid/liquid ratio increased from 5 to 30. The percentage yield increased from 17 mg/g to 55 mg/g. The maximum value of 55 mg/g total chlorogenic acid was obtained when the liquid/solid ratio, temperature, and extraction time were respectively controlled to be 30 g/g, 55° C. and 180 min.

4-caffeoylquinic acid (4-CQA)

By applying multiple regression analysis to the experimental data, the following second order polynomial equation was found to represent the extraction yield of 4-CQA (Y3): Y3=56.1268+−10.8746*A+8.03485*B+1.54769*C+2.90067*AB+−3.13905*AC+14.025*BC+−7.03086*A^2+−12.4312*B^2+−3.87252*C^2.

For 4-CQA, the Model F-value of 28.96 and associated P value of 0.0092 indicated that the regression model is significant. There is only a 0.92% chance that an F-value this large could occur due to noise. P-values less than 0.0500 indicate model terms are significant. In this case A, B, BC, A2, B2 are significant model terms. Values greater than 0.1000 indicate the model terms are not significant. The high value of R2 (0.9886) and adj-R2 (0.9545) indicated that the form of the model represented the actual relationship was well correlated between the response and independent variables. At the same time, a low value (7.73) of coefficient of the variation (CV) clearly indicated a high precision and a good reliability of the experimental values.

The three-dimensional (3-D) response surface and contour plots were the graphical representations of regression. It provided a method to visualize the relationship between responses and experimental levels of each variable parameters and the type of interactions between two test variables. In the response surface and contour plots, 4-CQA extraction yield was obtained along with two continuous variables while the other one was fixed constant at its zero level (center value of the testing ranges). From the sharp of the response surface, we also could see that the interaction was significant. When liquid/solid kept at optimum level, the extraction yield of 4-CQA increased with increase temperature. However, when temperature got over a certain value, the extraction yield decreased. It was because that high temperature could make 4-CQA decomposed. It showed that the 4-caffeoylquinic acid (4-CQA) could also decompose during a long time extraction when temperature is high. The longer extraction time needed when liquid/solid is higher. The maximum value of 62.97 mg/g 4-CQA was obtained when the liquid/solid ratio, temperature, and extraction time were respectively controlled to be 30 g/g, 55° C. and 180 min.

5-o-caffeoylquinic acid (5-CQA)

By applying multiple regression analysis to the experimental data, the following second order polynomial equation was found to represent the extraction yield of 5-CQA: Y5=29.6757+−5.48635*A+4.33813*B+1.65555*C+0.913624*AB+−1.1249*AC+7.59666*BC+−3.18214*A^2+−6.99323*B^2+−0.975141*C^2.

For 5-CQA, the Model F-value of 15.38 and associated P value of 0.0229 indicated that the regression model is significant. There is only a 2.29% chance that an F-value this large could occur due to noise. P-values less than 0.0500 indicate model terms are significant. In this case A, B, BC, B2 are significant model terms. Values greater than 0.1000 indicate the model terms are not significant. The high value of R2 (0.9788) and adj-R2 (0.9151) indicated that the form of the model represented the actual relationship was well correlated between the response and independent variables. At the same time, a low value (10.39) of coefficient of the variation (CV) clearly indicated a high precision and a good reliability of the experimental values.

The three-dimensional (3-D) response surface and contour plots were the graphical representations of regression. It provided a method to visualize the relationship between responses and experimental levels of each variable parameters and the type of interactions between two test variables. In the response surface and contour plots, 5-CQA extraction yield was obtained along with two continuous variables while the other one was fixed constant at its zero level (center value of the testing ranges). When liquid/solid kept at optimum level, the extraction yield of 5-CQA increased with increase temperature. However, when temperature got over a certain value, the extraction yield decreased. It showed that the 5-CQA could also decompose during a long time extraction. From the sharp of the response surface, we could see that the interaction was significant. Longer extraction time is needed for higher liquid/solid ratio. The maximum value of 35.3 mg/g 5-CQA was obtained when the liquid/solid ratio, temperature, and extraction time were respectively controlled to be 30 g/g, 55° C. and 180 min.

3,4-dicaffeoylquinic acid (3,4-diCQA)

By applying multiple regression analysis to the experimental data, the following second order polynomial equation was found to represent the extraction yield of 3,4-diCQA: Y6=10.6223+−1.84482*A+1.54172*B+0.451434*C+0.593569*AB+−0.513514*AC+2.64981*BC+−1.5156*A^2+−2.4587*B^2+−0.787695*C^2.

For 3,4-CQA, the Model F-value of 30.46 and associated P value of 0.0085 indicated that the regression model is significant. There is only a 0.85% chance that an F-value this large could occur due to noise. PP-values less than 0.0500 indicate model terms are significant. In this case A, B, BC, A2, B2 are significant model terms. Values greater than 0.1000 indicate the model terms are not significant. The high value of R2 (0.9892) and adj-R2 (0.9567) indicated that the form of the model represented the actual relationship was well correlated between the response and independent variables. At the same time, a low value (7.59) of coefficient of the variation (CV) clearly indicated a high precision and a good reliability of the experimental values.

The three-dimensional (3-D) response surface and contour plots were the graphical representations of regression. It provided a method to visualize the relationship between responses and experimental levels of each variable parameters and the type of interactions between two test variables. In the response surface and contour plots, 3,4-diCQA extraction yield was obtained along with two continuous variables while the other one was fixed constant at its zero level (center value of the testing ranges). When liquid/solid kept at optimum level, the extraction yield of 3,4-diCQA increased with increase temperature. However, when temperature got over a certain value, the extraction yield decreased. It was because that high temperature could make 3,4-diCQA decomposed. From the sharp of the response surface, we also could see that the interaction was significant. The liquid/solid ratio affected the extraction yield significantly. Longer extraction time is needed for higher liquid/solid ratio. The maximum value of 12 mg/g 3,4-diCQA was obtained when the liquid/solid ratio, temperature, and extraction time were respectively controlled to be 30 g/g, 55° C. and 180 min.

3,5-dicaffeoylquinic acid (3,5-diCQA)

By applying multiple regression analysis to the experimental data, the following second order polynomial equation was found to represent the extraction yield of 3,5-diCQA: Y7=47.4372+−8.25459*A+7.0397*B+2.14047*C+2.6516*AB+−1.99397*AC+11.9534*BC+−6.87771*A^2+−11.3866*B^2+−3.5024*C^2.

For 3,5-diCQA, the Model F-value of 41.20 and associated P value of 0.0055 indicated that the regression model is significant. There is only a 0.55% chance that an F-value this large could occur due to noise. P-values less than 0.0500 indicate model terms are significant. In this case A, B, BC, A2, B2 are significant model terms. Values greater than 0.1000 indicate the model terms are not significant. The high value of R2 (0.9920) and adj-R2 (0.9679) indicated that the form of the model represented the actual relationship was well correlated between the response and independent variables. At the same time, a low value (6.67) of coefficient of the variation (CV) clearly indicated a high precision and a good reliability of the experimental values.

The three-dimensional (3-D) response surface and contour plots were the graphical representations of regression. It provided a method to visualize the relationship between responses and experimental levels of each variable parameters and the type of interactions between two test variables. In the response surface and contour plots, 3,5-diCQA extraction yield was obtained along with two continuous variables while the other one was fixed constant at its zero level (center value of the testing ranges). When liquid/solid kept at optimum level, the extraction yield of 3,5-diCQA increased with increase temperature. However, when temperature got over a certain value, the extraction yield decreased. It was because that high temperature could make 3,4-diCQA decomposed. From the sharp of the response surface, we also could see that the interaction was significant. The liquid/solid ratio affected the extraction yield significantly. Longer extraction time is needed for higher liquid/solid ratio. The maximum value of 21.5 mg/g 3,5-diCQA was obtained when the liquid/solid ratio, temperature, and extraction time were respectively controlled to be 30 g/g, 55° C. and 180 min.

4,5-dicaffeoylquinic acid (4,5-diCQA)

By applying multiple regression analysis to the experimental data, the following second order polynomial equation was found to represent the extraction yield of 4,5-CQA: Y8=18.5102+−3.19188*A+2.66662*B+1.09715*C+1.18942*AB+−0.661707*AC+4.76348*BC+−2.10181*A^2+−4.56793*B^2+−1.05986*C^2.

For 4,5-diCQA, the Model F-value of 59.61 and associated P value of 0.0032 indicated that the regression model is significant. There is only a 0.32% chance that an F-value this large could occur due to noise. P-values less than 0.0500 indicate model terms are significant. In this case A, B, C, AB, BC, $A^2$, $B^2$ are significant model terms. Values greater than 0.1000 indicate the model terms are not significant. The high value of R2 (0.9944) and adj-R2 (0.9798) indicated that the form of the model represented the actual relationship was well correlated between the response and independent variables. At the same time, a low value (5.41) of coefficient of the variation (CV) clearly indicated a high precision and a good reliability of the experimental values.

The three-dimensional (3-D) response surface and contour plots were the graphical representations of regression. It provided a method to visualize the relationship between responses and experimental levels of each variable parameters and the type of interactions between two test variables. In the response surface and contour plots, 4,5-diCQA extraction yield was obtained along with two continuous variables while the other one was fixed constant at its zero level (center value of the testing ranges). When liquid/solid kept at optimum level, the extraction yield of 4,5-diCQA increased with increase temperature. However, when temperature got over a certain value, the extraction yield decreased. It was because that high temperature could make 4,5-diCQA decomposed. From the sharp of the response surface, we also could see that the interaction was significant. The liquid/solid ratio affected the extraction yield significantly. Longer extraction time is needed for higher liquid/solid ratio. The maximum value of 54 mg/g 4,5-diCQA was obtained when the liquid/solid ratio, temperature, and extraction time were respectively controlled to be 30 g/g, 55° C. and 180 min.

Rutin

By applying multiple regression analysis to the experimental data, the following second order polynomial equation was found to represent the extraction yield of Rutin: Y9=8.59949+−2.02475*A+−0.432504*B+0.134262*C+0.45758*AB+−0.516049*AC+2.16226*BC+−1.87299*A^2+−3.01976*B^2+−0.610253*C^2.

For rutin, the Model F-value of 33.40 and associated P value of 0.0075 indicated that the regression model is significant. P-values less than 0.0500 indicate model terms are significant. In this case A, BC, A2, B2 are significant model terms. Values greater than 0.1000 indicate the model terms are not significant. The high value of R2 (0.9901) and adj-R2 (0.9605) indicated that the form of the model represented the actual relationship was well correlated between the response and independent variables. At the same time, a low value (9.84) of coefficient of the variation (CV) clearly indicated a high precision and a good reliability of the experimental values.

The three-dimensional (3-D) response surface and contour plots were the graphical representations of regression. It provided a method to visualize the relationship between responses and experimental levels of each variable parameters and the type of interactions between two test variables. In the response surface and contour plots, 4-CQA extraction yield was obtained along with two continuous variables while the other one was fixed constant at its zero level (center value of the testing ranges). When liquid/solid kept at optimum level, the extraction yield of rutin increased with increase temperature. However, when temperature got over a certain value, the extraction yield decreased. It was because that high temperature could make rutin decomposed. Longer extraction time would also cause rutin decomposed. From the sharp of the response surface, we also could see that the interaction was significant. The liquid/solid ratio affected the extraction yield significantly. The maximum value of 8.6 mg/g rutin was obtained when the liquid/solid ratio, temperature, and extraction time were respectively controlled to be 17.5 g/g, 55° C. and 120 min.

Theobromine

By applying multiple regression analysis to the experimental data, the following second order polynomial equation was found to represent the extraction yield of Theobromine: Y10=9.96722+−3.03923*A+3.69081*B+0.996837*C+−1.61736*AB+1.3461*AC+3.1009*BC+−2.5968*A^2+−0.983486*B^2+−0.320714*C^2.

For Theobromine, The Model F-value of 4.90 implies the model is not significant relative to the noise. There is a 10.91% chance that an F-value this large could occur due to noise. So the model reduced to linear as represented by: Y10=7.56661+−3.03923*A+3.69081*B+0.996837*C.

The Model F-value of 6.27 implies the model is significant. There is only a 1.39% chance that an F-value this large could occur due to noise. P-values less than 0.0500 indicate model terms are significant. In this case A, B are significant model terms. The value of R2 (0.9363) and adj-R2 (0.7451) indicated that the form of the model represented the actual relationship was well correlated between the response and independent variables.

The three-dimensional (3-D) response surface and contour plots were the graphical representations of regression. It provided a method to visualize the relationship between responses and experimental levels of each variable parameters and the type of interactions between two test variables. In the response surface and contour plots, Theobromine extraction yield was obtained along with two continuous variables while the other one was fixed constant at its zero level (center value of the testing ranges). When temperature kept at optimum level, the extraction yield of theobromine increased with increase liquid/solid ratio. The maximum value of 16.5 mg/g Theobromine was obtained when the liquid/solid ratio, temperature, and extraction time were respectively controlled to be 30 g/g, 55° C. and 180 min.

Caffeine

By applying multiple regression analysis to the experimental data, the following second order polynomial equation was found to represent the extraction yield of Caffeine:

Y11=20.9522+−3.31823*A+2.72458*B+1.05134*C+1.35799*AB+−0.56039*AC+5.43106*BC+−2.51197*A^2+−5.37211*B^2+−1.51228*C^2.

For caffeine, the Model F-value of 24.58 and associated P value of 0.0117 indicated that the regression model is significant. P-values less than 0.0500 indicate model terms are significant. In this case A, B, BC, B2 are significant model terms. P-values less than 0.0500 indicate model terms are significant. In this case A, BC, A2, B2 are significant model terms. Values greater than 0.1000 indicate the model terms are not significant. The high value of R2 (0.9866) and adj-R2 (0.9465) indicated that the form of the model represented the actual relationship was well correlated between the response and independent variables. At the same time, a low value (8.31) of coefficient of the variation (CV) clearly indicated a high precision and a good reliability of the experimental values.

The three-dimensional (3-D) response surface and contour plots were the graphical representations of regression. It provided a method to visualize the relationship between responses and experimental levels of each variable parameters and the type of interactions between two test variables. In the response surface and contour plots, caffeine extraction yield was obtained along with two continuous variables while the other one was fixed constant at its zero level (center value of the testing ranges). Caffeine is relatively stable with higher extraction temperature, but the extraction yield of caffeine increased with increase liquid/solid ratio, and when it got over a certain value, the extraction yield decreased. It was because that long extraction time could decompose caffeine. The sharp shape of surface indicate that interaction is significant. The maximum value of 23 mg/g caffeine was obtained when the liquid/solid ratio, temperature, and extraction time were respectively controlled to be 30 g/g, 55° C. and 180 min.

Optimum conditions for the extraction process were intended to obtain maximum extraction yield as well as higher total chlorogenic acids content. Based on the above findings, an optimization study was performed and the optimal conditions were determined as follows: extraction temperature of 55° C., extraction time of 180 min and liquid/solid ratio of 30. Triple validating experiments were conducted to confirm the prediction. The extraction yield and total chlorogenic acids content were 78±2% and 240±3.2 mg/g respectively, which were approximately equal to the predicted yield (77.8%) and total chlorogenic acids content (241 mg/g) by the regression models.

TABLE 10

$IC_{50}$ values of experimental samples

| solvent | $IC_{50}$ (μg/ml) |
|---|---|
| 3,5-diCQA | 185.68 |
| 4,5-diCQA | 199.68 |
| 3-CQA | 258.81 |
| rutin | 246.76 |
| ascorbic acid | 446.70 |
| water | 610.00 |
| 20% ethanol | 322.43 |
| 40% ethanol | 495.00 |
| 60% ethanol | 436.91 |
| 80% ethanol | 590.41 |
| ethanol | 1696.60 |
| citglu2:1 | 252.00 |
| citglu1:1 | 263.00 |
| citglu1:2 | 310.00 |
| citsuc2:1 | 256.00 |
| citsuc1:1 | 280.00 |
| citsuc1:2 | 510.00 |
| clcit3:1 | 436.91 |
| clcit3:1 | 290.42 |
| clcit3:1 | 282.81 |
| clcit3:1 | 322.43 |
| clcit3:1 | 315.00 |
| clcit3:1 | 320.00 |
| clcit3:1 | 290.38 |
| clcit3:1 | 297.77 |
| clcit3:1 | 64.95 |
| clcit3:1 | 375.19 |
| clcit3:1 | 311.32 |
| clcit3:1 | 148.35 |
| clcit3:1 | 81.10 |
| clcit3:1 | 416.50 |
| clcit3:1 | 140.94 |

The yerba mate extraction obtained at different conditions were subjected to DPPH radical scavenging assay to investigate the antioxidant capacity. DPPH assay is selected as it is a promising way to indicate the presence of antioxidant compounds. The assay is easy and low cost since the radical compounds is relatively stable and need not be generated. Remarkably, all the tested antioxidant-loaded NaDES solution exhibited a higher antioxidant potential than the antioxidant in aqueous form. The DPPH assay showed that the highest antioxidant activity was obtained at aqueous chlorine chloride/citric acid and it is highly correlated with the higher content of chlorogenic acids. Greater antioxidant activity can be attributed to one of the components of NaDES system, citric acid. Citric acid is well known natural antioxidant due to its capability in scavenging free radical species (ROS). The inclusion of citric acid may contribute to the increased antioxidant activity of antioxidant-CHCL/citric acid NaDES system. This fits into our hypothesis of the role of NaDES. Another notable finding is that the antioxidant activity of CHCL/citric acid NaDES system with 30 wt %, 50 wt % and 80 wt % of water content slightly outperformed the pure CHCL/citric acid NaDES system. This phenomenon is coherent with the effect of viscosity on the solubility of antioxidant compounds. It implies that the physicochemical properties of NaDES may exert a big effect on the antioxidant activity. Given this information, it can be concluded that CHCL/CA NaDES system with 50 wt % water shows an excellent ability in improving the antioxidant activity, which once again highlights its potential in food, nutraceutical and pharmaceutical industry.

Example 5: Extraction of Theobromine

The following example demonstrates extraction of theobromine using the methods and compositions described herein.

Yerba mate leaves were obtained, and theobromine was extracted using NaDES. In particular, a variety of NaDES were used for theobromine extraction, as set forth in Table 11.

TABLE 11

Yerba Mate Extraction with NaDES

| NaDES System | NaDES | Mole Ratio |
|---|---|---|
| Sugar-Based | Glucose:Sucrose | 1:1 |
| | Glucose:Fructose | 1:1 |
| Organic Acid-Based | Citric Acid:Glucose | 1:1 |
| | Citric Acid:Sucrose | 1:1 |
| | Citric Acid:Fructose | 1:1 |
| Choline Chloride-Based | Choline Chloride:Citric Acid | 1:1 |
| | Choline Chloride:Glucose | 1:1 |
| | Choline Chloride:Sucrose | 1:1 |
| Polyol-Based | Erythritol:Choline Chloride | 1:1 |
| | Erythritol:Citric Acid | 1:1 |
| | Erythritol:Glucose:Fructose | 1:1:1 |

Figure 7:
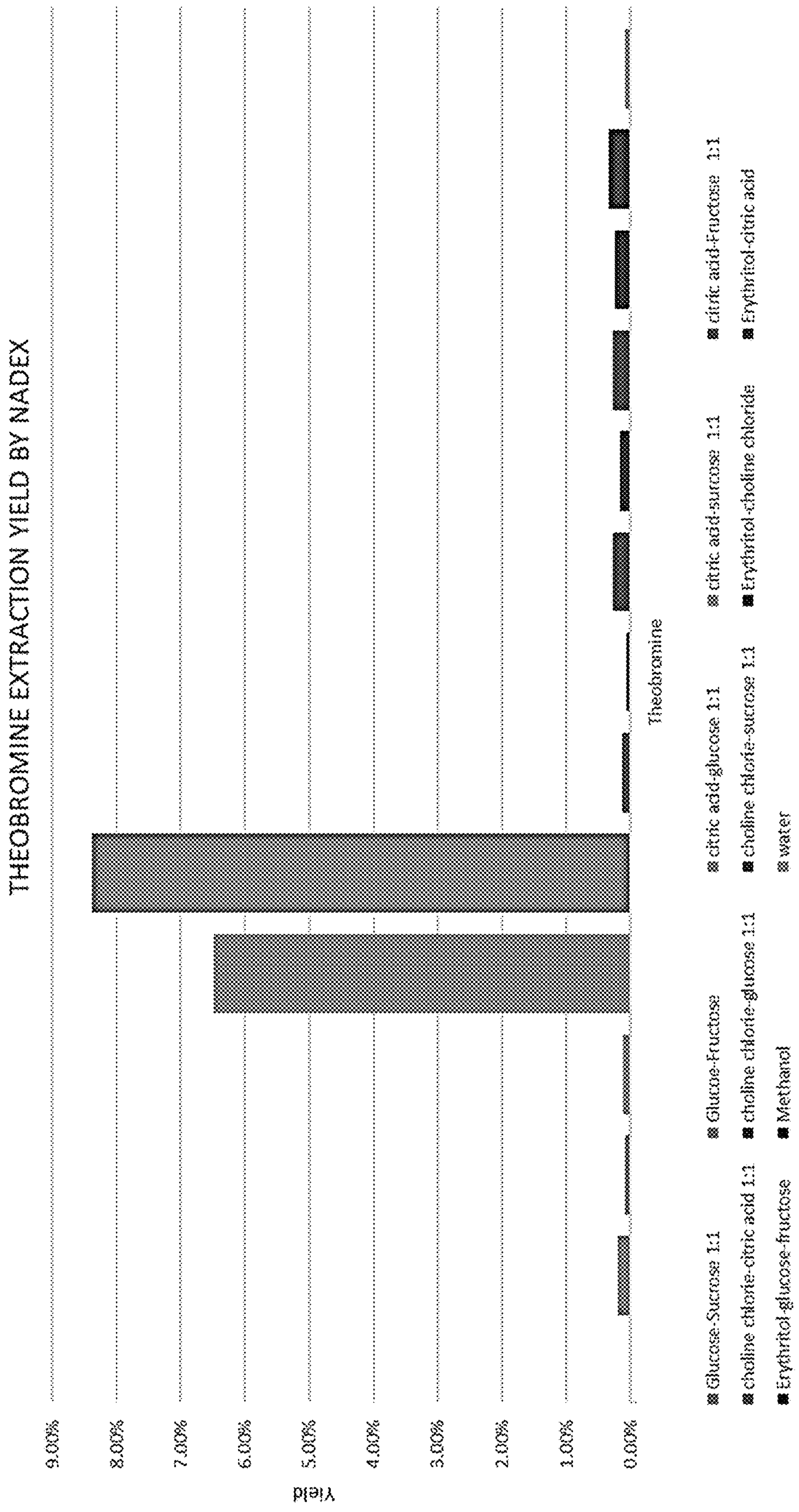
FIG. 7 depicts a bar graph showing extraction yield of theobromine using a variety of NaDES systems, including, from left to right: glucose:sucrose, glucose:fructose, citric acid:glucose, citric acid:sucrose, citric acid:fructose, choline chloride:citric acid, choline chloride:glucose, choline chloride:sucrose, erythritol:choline chloride, erythritol:citric acid, erythritol:glucose:fructose, methanol, and water, each present in a 1:1 ratio (where relevant).

As shown in FIG. 7, the extraction yield of theobromine from yerba mate leaves by citric acid:sucrose and citric acid:fructose was 6.50% and 8.39% (fourth and fifth bar from the left in FIG. 7), respectively, significantly higher than extraction yield with the other NaDES system and water (far right in FIG. 7). Theobromine extraction yield by water was 0.08%-0.75%. The combination of citric acid with fructose or sucrose (glucose and fructose in the ratio of 1:1) improved theobromine extraction yield 10-20 times, in comparison to water, very likely due to an increased ability of theobromine to form hydrogen bonds with these NaDES. However, no such observation was found in citric acid-glucose.

Jeliński et al. studied the solubility of pure theobromine in various solvents and NaDES (Jeliński et al., 2021). The authors reported that the solubility of theobromine in choline chloride and glycerol was almost 32 times larger than in water; the solubility of theobromine in choline chloride with glucose and fructose was almost similar. Interestingly there was no correlation between the solubility of theobromine in the NaDES reported in the literature and the extractability of theobromine from the yerba mate leaves with the NaDES described herein, implying the matrix effect in extraction. Thus, these results were unexpected and surprising.

As shown in this example, theobromine extraction yield reached about 8-9% by weight from yerba mate leaves, which has never previously been obtained. These studies were performed in triplicate, with repeatable observation and results. The particular combination of citric acid with fructose or sugar containing fructose, such as sucrose, shows remarkable selectivity for theobromine. This particular NaDES system is also beneficial for extracting other botanicals rich in theobromine, such as cacao.

All headings are for the convenience of the reader and should not be used to limit the meaning of the text that follows the heading, unless so specified.

All patents and publications mentioned in the specification are indicative of the levels of those skilled in the art to which the invention pertains. All patents and publications are herein incorporated by reference to the same extent as if each individual publication was specifically and individually indicated to be incorporated by reference, and for any disclosure specifically referenced herein.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the claims.

REFERENCES

The following references are expressly incorporated herein by reference in their entireties for all purposes.

Abbott, A. P., Boothby, D., Capper, G., Davies, D. L., & Rasheed, R. K. (2004). Deep Eutectic Solvents Formed between Choline Chloride and Carboxylic Acids: Versatile Alternatives to Ionic Liquids. Journal of the American Chemical Society, 126(29), 9142-9147.

Abbott, A. P., Capper, G., Davies, D. L., Rasheed, R. K., & Tambyrajah, V. (2003). Novel solvent properties of choline chloride/urea mixtures. Chemical Communications, 1, 70-71.

Bastos, D. H. M., De Oliveira, D. M., Matsumoto, R. L. T., Carvalho, P. de O., & Ribeiro, M. L. (2007). Yerba mate: pharmacological properties, research and biotechnology. Med Aromat Plant Sci Biotechnol, 1(1), 37-46.

Bojić, M., Simon Haas, V., Šariĉ, D., & Maleš, Ž. (2013). Determination of flavonoids, phenolic acids, and xanthines in mate tea (*Ilex paraguariensis* St.-Hil.). Journal of Analytical Methods in Chemistry, 2013.

Burris, K. P., Harte, F. M., Davidson, P. M., Stewart Jr, C. N., & Zivanovic, S. (2012). Composition and bioactive properties of yerba mate (*Ilex paraguariensis* A. St.-Hil.): a review. Chilean Journal of Agricultural Research, 72(2), 268.

Chandrasekara, A., & Shahidi, F. (2018). Herbal beverages: Bioactive compounds and their role in disease risk reduction-A review. Journal of Traditional and Complementary Medicine, 8(4), 451-458.

Chianese, G., Golin-Pacheco, S. D., Taglialatela-Scafati, O., Collado, J. A., Munoz, E., Appendino, G., & Pollastro, F. (2019). Bioactive triterpenoids from the caffeine-rich plants guayusa and maté. Food Research International, 115, 504-510.

Choi, Y. H., van Spronsen, J Dai, Y., Verberne, M., Hollmann, F., Arends, I. W. C. E., Witkamp, G.-J., & Verpoorte, R. (2011). Are Natural Deep Eutectic Solvents the Missing Link in Understanding Cellular Metabolism and Physiology? Plant Physiology, 156(4), 1701-1705.

Croge, C. P., Cuquel, F. L., & Pintro, P. T. M. (2020). Yerba mate: cultivation systems, processing and chemical composition. A review. Scientia Agricola, 78(5).

Dai, Y. (2006). Natural deep eutectic solvents and their application in natural product research and. Carbohydr. Polym, 66, 546-550.

Dai, Y. (2007). Natural deep eutectic solvents and their application in natural product research and. Plant J, 50, 967-981.

Dai, Y., Witkamp, G.-J., Verpoorte, R., & Choi, Y. H. (2013). Natural Deep Eutectic Solvents as a New Extraction Media for Phenolic Metabolites in Carthamus tinctorius L. Analytical Chemistry, 85(13), 6272-6278.

Ferreira Cuelho, C. H., de França Bonilha, I., Scotti do Canto, G., & Palermo Manfron, M. (2015). Recent advances in the bioactive properties of yerba mate. Revista Cubana de Farmacia, 49(2), 375-383.

Frizon, C. N. T., Perussello, C. A., Sturion, J. A., & Hoffmann-Ribani, R. (2018). Novel Beverages of Yerba-Mate and Soy: Bioactive Compounds and Functional Properties. Beverages, 4(1), 21.

Heck, C. I., & De Mejia, E. G. (2007). Yerba Mate Tea (*Ilex paraguariensis*): a comprehensive review on chemistry, health implications, and technological considerations. Journal of Food Science, 72(9), R138-R151.

Isolabella, S., Cogoi, L., López, P., Anesini, C., Ferraro, G., & Filip, R. (2010). Study of the bioactive compounds variation during yerba mate (*Ilex paraguariensis*) processing. Food Chemistry, 122(3), 695-699.

Jeliński, T. et al. (2021) 'Experimental and Theoretical Study on Theobromine Solubility Enhancement in Binary Aqueous Solutions and Ternary Designed Solvents.', Pharmaceutics, 13(8). doi: 10.3390/pharmaceutics13081118.

Junior, E. L. C., & Morand, C. (2016). Interest of mate (*Ilex paraguariensis* A. St.-Hil.) as a new natural functional food to preserve human cardiovascular health—A review. Journal of Functional Foods, 21, 440-454.

Liu, Y., Friesen, J. B., McAlpine, J. B., Lankin, D. C., Chen, S. N., & Pauli, G. F. (2018). Natural Deep Eutectic Solvents: Properties, Applications, and Perspectives. Journal of Natural Products, 81(3), 679-690.

Matei, M. F., Jaiswal, R., Patras, M. A., & Kuhnert, N. (2016). LC-MSn study of the chemical transformations of hydroxycinnamates during yerba maté (*Ilex paraguariensis*) tea brewing. Food Research International, 90, 307-312.

Oellig, C., Schunck, J., & Schwack, W. (2018). Determination of caffeine, theobromine and theophylline in Mate beer and Mate soft drinks by high-performance thin-layer chromatography. Journal of Chromatography A, 1533, 208-212.

Puangpraphant, S. (2012). Anti-inflammatory and anti-colon cancer potential of yerba mate (*Ilex paraguariensis* St. Hilaire) bioactive constituents. University of Illinois at Urbana-Champaign.

Riachi, L. G., Simas, D. L. R., Coelho, G. C., Marcellini, P. S., da Silva, A. J. R., & de Maria, C. A. B. (2018). Effect of light intensity and processing conditions on bioactive compounds in maté extracted from yerba mate (*Ilex paraguariensis* A. St.-Hil.). Food Chemistry, 266, 317-322.

Shen, Q., Zhang, B., Xu, R., Wang, Y., Ding, X., & Li, P. (2010). Antioxidant activity in vitro of the selenium-contained protein from the Se-enriched *Bifidobacterium animalis* 01. Anaerobe, 16(4), 380-386.

Souza, A. H. P., Correa, R. C. G., Barros, L., Calhelha, R. C., Santos-Buelga, C., Peralta, R. M., Bracht, A., Matsushita, M., & Ferreira, I. C. F. R. (2015). Phytochemicals and bioactive properties of *Ilex paraguariensis*: An in-vitro comparative study between the whole plant, leaves and stems. Food Research International, 78, 286-294.

What is claimed is:

1. A method of isolating a plant extract from a plant material, the method comprising: obtaining a plant material; processing the plant material; mixing the processed plant material with a natural deep eutectic solvent (NaDES); and isolating a plant extract; wherein the plant material is obtained from yerba mate; wherein the NaDES comprises choline chloride and citric acid present in a ratio of 3:1, and water present in an amount of 50%.

2. The method of claim 1, wherein the plant extract is a xanthine alkaloid, chlorogenic acid, or matesponin.

3. The method of claim 2, wherein the xanthine alkaloid comprises caffeine, theobromine, theophylline, or an analogue or derivative thereof.

4. The method of claim 2, wherein the chlorogenic acid comprises caffeic acid, tannin, or an analogue or derivative thereof.

5. The method of claim 1, further comprising heating, stirring, centrifuging, and/or filtering following the mixing step.

6. The method of claim 1, wherein the plant extract is theobromine, extracted in an amount ranging from about 5% to about 10% by weight.

7. A composition comprising: botanical isolates from yerba mate; and a natural deep eutectic solvent (NaDES), wherein the NaDES comprises choline chloride and citric acid present in a ratio of 3:1, and water present in an amount of 50%.

8. The composition of claim 7, wherein the botanical isolates comprise a xanthine alkaloid, chlorogenic acid, or matesponin.

9. The composition of claim 7, wherein the botanical isolates comprise comprises caffeine, theobromine, theophylline, caffeic acid, tannin, or an analogue or derivative thereof.

10. The composition of claim 7, wherein the NaDES comprises choline chloride, citric acid, erythritol, glucose, sucrose, fructose, or a combination thereof.

* * * * *